United States Patent
Zhang et al.

(10) Patent No.: US 8,617,082 B2
(45) Date of Patent: Dec. 31, 2013

(54) HEART SOUNDS-BASED PACING OPTIMIZATION

(75) Inventors: Xusheng Zhang, Shoreview, MN (US); Aleksandre T. Sambelashvili, Maple Grove, MN (US); David A. Anderson, Stanchfield, MN (US); Zhendong Song, Medina, MN (US)

(73) Assignee: Medtronic, Inc., Minneapolis, MN (US)

( * ) Notice: Subject to any disclaimer, the term of this patent is extended or adjusted under 35 U.S.C. 154(b) by 154 days.

(21) Appl. No.: 13/111,260

(22) Filed: May 19, 2011

(65) Prior Publication Data

US 2012/0296228 A1    Nov. 22, 2012

(51) Int. Cl.
*A61B 5/02*    (2006.01)

(52) U.S. Cl.
USPC .......................................................... 600/528

(58) Field of Classification Search
USPC ................................................. 600/528, 514
See application file for complete search history.

(56) References Cited

U.S. PATENT DOCUMENTS

| | | | |
|---|---|---|---|
| 4,374,382 A | 2/1983 | Markowitz | |
| 5,117,824 A | 6/1992 | Keimel et al. | |
| 5,545,186 A | 8/1996 | Olson et al. | |
| 5,755,736 A | 5/1998 | Gillberg et al. | |
| 6,393,316 B1 | 5/2002 | Gillberg et al. | |
| 6,449,508 B1 | 9/2002 | Sheldon et al. | |
| 6,643,548 B1 | 11/2003 | Mai et al. | |
| 7,123,962 B2 | 10/2006 | Siejko et al. | |
| 7,139,609 B1 | 11/2006 | Min et al. | |
| 7,209,786 B2 * | 4/2007 | Brockway et al. | 607/17 |
| 7,212,849 B2 | 5/2007 | Zhang et al. | |
| 7,248,923 B2 | 7/2007 | Maile et al. | |
| 7,343,915 B2 | 3/2008 | Addington et al. | |
| 7,460,909 B1 | 12/2008 | Koh et al. | |
| 7,689,283 B1 | 3/2010 | Schecter | |
| 7,787,946 B2 | 8/2010 | Stahmann et al. | |
| 2004/0220636 A1 | 11/2004 | Burnes | |
| 2005/0080461 A1 | 4/2005 | Stahmann et al. | |
| 2007/0049977 A1 | 3/2007 | Von Arx et al. | |
| 2007/0123943 A1 | 5/2007 | Patangay et al. | |
| 2007/0142866 A1 | 6/2007 | Li et al. | |
| 2007/0150014 A1 | 6/2007 | Kramer et al. | |
| 2007/0150017 A1 | 6/2007 | Salo | |
| 2008/0051839 A1 | 2/2008 | Libbus et al. | |
| 2008/0082018 A1 | 4/2008 | Sackner et al. | |
| 2008/0103399 A1 | 5/2008 | Patangay et al. | |
| 2008/0195168 A1 | 8/2008 | Arand et al. | |
| 2008/0234594 A1 | 9/2008 | Brooks et al. | |
| 2008/0275349 A1 | 11/2008 | Halperin et al. | |
| 2008/0294213 A1 | 11/2008 | Holmstrom et al. | |
| 2009/0048640 A1 | 2/2009 | Bauer et al. | |

(Continued)

OTHER PUBLICATIONS

U.S. Appl. No. 13/114,838, by Zhang et al., filed May 24, 2011.

(Continued)

*Primary Examiner* — Amanda Patton
(74) *Attorney, Agent, or Firm* — Reed A. Duthler

(57) ABSTRACT

An implantable medical device receives both heart sound and electrogram signals. A processor within the implantable medical device extracts physiologically relevant information from both the heart sound signal and the electrogram signal. Based on the extracted physiologically relevant information a set of pacing parameters is evaluated. In certain examples, the values of the pacing parameters may be changed by the implantable medical device in response to the physiologically relevant information extracted from the heart sound signal and the electrogram signal.

38 Claims, 12 Drawing Sheets

(56) References Cited

U.S. PATENT DOCUMENTS

| | | | |
|---|---|---|---|
| 2009/0131999 | A1 | 5/2009 | Li et al. |
| 2009/0216138 | A1 | 8/2009 | Arand |
| 2009/0254139 | A1 | 10/2009 | Bjorling |
| 2010/0023078 | A1 | 1/2010 | Dong et al. |
| 2010/0069768 | A1 | 3/2010 | Min et al. |
| 2010/0073170 | A1 | 3/2010 | Siejko et al. |
| 2010/0087746 | A1* | 4/2010 | Radzievsky et al. ......... 600/528 |
| 2010/0185109 | A1 | 7/2010 | Zhang et al. |
| 2010/0198308 | A1 | 8/2010 | Zhou et al. |
| 2010/0312130 | A1 | 12/2010 | Zhang et al. |
| 2010/0331903 | A1 | 12/2010 | Zhang et al. |
| 2011/0015535 | A1 | 1/2011 | Lange et al. |
| 2011/0015703 | A1 | 1/2011 | Ternes et al. |
| 2011/0015704 | A1 | 1/2011 | Ternes et al. |
| 2011/0087079 | A1 | 4/2011 | Aarts |

OTHER PUBLICATIONS

Stec et al., "Premature ventricular complex-induced chronic cough and cough syncope," Eur Respir J. 2007:30 (2):391-394.

Toggweiler et al., "Visualizing Pacemaker-Induced Phrenic Nerve Stimulation with Acoustic Cardiography," PACE 2007; 30:806-807.

Zuber et al., "Detection and Hemodynamic Significance of Cardiac Pacemaker-Induced Phrenic Nerve Stimulation," Congest Heart Fail. 2010:16:147-152.

Stahlberg et al., "Cardiac output response to changes of the atrioventricular delay in different body positions and during exercise in patients receiving cardiac resynchronization therapy," Europace (2009) 11: 1160-1167.

Zuber et al., "Systolic Dysfunction: Correlation of Acoustic Cardiography With Doppler Echocardiography," CHF. 2006; 12(4 supple 1): 14-18.

Auricchio et al., "Effect of Pacing Chamber and Atrioventricular Delay on Acute Systolic Function of Paced Patients With Congestive Heart Failure," Circulation 1999;99:2993-3001.

Baker, II et al., "Acute Evaluation of Programmer-Guided AV/PV and VV Delay Optimization Comparing an IEGM Method and Echocardiogram for Cardiac Resynchronization Therapy in Heart Failure Patients and Dual-Chamber ICD Implants," J Cardiovasc Electrophysiol, vol. 18, pp. 1-7, Jan. 2007.

Gold et al., "A Prospective Comparison of AV Delay Programming Methods for Hemodynamic Optimization during Cardiac Resynchronization Therapy," J Cardiovasc Electrophysiol, vol. 18, pp. 1-7, May 2007.

Gras et al., "Optimization of AV and VV Delays in the Real-World CRT Patient Population: An International Survey on Current Clinical Practice," PACE 2009;32:S236-23.

O'Donnell et al., "Long-Term Variations in Optimal Programming of Cardiac Resynchronization Therapy Devices," PACE 2005;28:S24-26.

Erne, "Beyond auscultation-acoustic cardiography in the diagnosis and assessment of cardiac disease," Swiss Med Wkly 2008;138(31-32):439-452.

U.S. Appl. No. 13/474,041, by Zhang et al., filed May 17, 2012.
U.S. Appl. No. 13/474,074, by Zhang et al., filed May 17, 2012.
U.S. Appl. No. 13/360,149, by Anderson et al., filed Jan. 27, 2012.

* cited by examiner

HEART SOUNDS-BASED PACING OPTIMIZATION

TECHNICAL FIELD

The disclosure relates to cardiac pacing therapy.

BACKGROUND

Implantable pacemakers improve cardiac function by improving electrical activation of the heart. It has been demonstrated that the degree of improvement in cardiac function may depend on the locations of pacing sites, vector configuration, and the programmable parameters that control the timing of pacing pulse. Cardiac function is quantified by, for example, cardiac output and filling pressures. In general, the use of implantable pacemakers to improve cardiac function is referred to as cardiac resynchronization therapy (CRT) and implemented using a biventricular cardiac pacemaker that can pace both the right and left ventricle. The pacemaker is able to resynchronize a heart, whose right and left ventricles do not contract in synchrony, by pacing both the right and left ventricles. Biventricular pacemakers have at least two leads, one in the right ventricle to stimulate the septum, and the other inserted through the coronary sinus to pace the lateral wall of the left ventricle. An additional lead in the right atrium can facilitate synchrony with atrial contraction.

Programmable biventricular pacemakers enable optimization of treatment for a particular patient. The various time delays between pacemaker timing pulses can be adjusted and set for each patient. The optimization procedure generally requires a physician or nurse to set delays between various timing pulses. The purpose of the optimization is to coordinate contraction of the various chambers in response to the various cardiac pulses to improve overall efficiency and function of the heart. Adjustment of atrioventricular (AV) pacing delays allows optimization of the time interval between paced or intrinsic atrial contraction and the paced ventricular beat for best cardiac efficiency. It is generally believed that both ventricles should contract simultaneously for optimum cardiac performance; however, interventricular (VV) pacing delay is often also required to obtain contraction. While optimal pacing sites and pacing parameters can provide the largest improvement in cardiac function, the parameters are patient-specific and may change over time.

Most commonly, optimization of pacing parameters is done during follow up visits using echocardiography. Parameters that determine timing, such as AV delay and VV delay are programmed to different values, and at each setting a particular echocardiographic index is measured. In many commercial pacemakers, a wireless communication system allows for this external programming. Generally, the pacemaker includes a short range telemetry module that communicates with an external device to facilitate communications with the implanted pacemaker.

Echocardiographic optimization is subject to a number of problems. For example, it is time and resource consuming. In addition, echocardiographic optimization may have limited reproducibility and greater inter- and intra-operator variability. Further, echocardiography is ordinarily used to optimize settings only when a patient is at rest. For these reasons, some clinicians may not routinely perform optimization. Moreover, using echocardiographic optimization, there still may be numerous patients who are non-responders to the therapy.

SUMMARY

In general, the disclosure describes techniques for CRT optimization of an implantable medical device (IMD). More specifically, the disclosure describes techniques for adaptive and ambulatory optimization of pacing parameters in an IMD using heart sound and electrogram (EGM) signals obtained by the IMD.

In one example, the disclosure is directed to a method in which heart sounds are obtained from an implanted heart sound sensor and the EGM is obtained from electrodes of an implantable device. One or more acoustic cardiographic metrics are generated based on at least one of the heart sounds and the EGM for a set of cardiac pacing parameters. Each of the cardiac pacing parameters having a value. The various acoustic cardiographic metrics may indicate an electrical or mechanical dysfunction of the heart. The acoustic cardiographic metric can be, for example, an indication of atrioventricular (AV) dyssynchrony based on an interval from heart sound S2 to heart sound S1. Another possible acoustic cardiographic metric is an indication of interventricular (VV) dyssynchrony that is determined based on a splitting of at least one of heart sound S1 and heart sound S2. An acoustic cardiographic metric that is an indication of left interventricular dyssynchrony may be based on one or more of electromechanical activation delay (EMAT), aortic pre-ejection interval, heart sound M1 duration, and heart sound A2 duration. EMAT and the aortic pre-ejection interval are based on an interval between the Q-wave of an EGM or the R-wave of an EGM and the S1 heart sound. Another acoustic cardiographic metric is a surrogate for a myocardial performance index (MPI) that is based on at least a duration of heart sound S1 and a duration of heart sound S2.

In another example, the disclosure is directed to a method including delivering CRT using an IMD in a patient. Heart sounds signals are monitored using a heart sound sensor implanted within the patient. EGM signals are monitored using electrodes of the implantable medical device. The method further includes evaluating at least one heart sounds metric. The heart sounds metric may include one or more of: heart sound S1 splitting and heart sounds S2 splitting; relative intensity in M1 and T1; the A2 to P2 amplitude ratio; variability in Q-wave to A2 intervals or heart sound S4. Based on the evaluation of the one or more heart sound metrics, an indication that the patient is suffering from systematic or pulmonary hypertension is generated.

In another example, the disclosure is directed to a method including delivering CRT using an IMD in a patient using a set of cardiac pacing parameter values. Heart sound signals are monitored using a heart sound sensor implemented with the IMD and EGM signals are monitored using electrodes of the IMD. At least one of the set of cardiac pacing parameter values is evaluated. The evaluation is based on at least one acoustic cardiographic metric and the evaluation includes varying the value of the cardiac pacing parameter over a predetermined range at a predetermined interval. In response to variation in the cardiac pacing parameter value, the value of the acoustic cardiographic metric corresponding to each value of the cardiac pacing parameter is stored. The various acoustic cardiographic metrics may indicate an electrical or mechanical dysfunction of the heart. The acoustic cardiographic metric can be, for example, an indication of atrioventricular (AV) dyssynchrony based on an interval from heart sound S2 to heart sound S1. Another possible acoustic cardiographic metric is an indication of interventricular (VV) dyssynchrony that is determined based on a splitting of at least one of heart sound S1 and heart sound S2. An acoustic cardiographic metric that is an indication of left interventricular dyssynchrony may be based on one or more of electromechanical activation delay (EMAT) plus S1 duration, heart sound M1 duration, and heart sound A2 duration. EMAT and the aortic pre-ejection interval are based on an interval between the Q-wave of an EGM or the R-wave of an EGM and the S1 heart sound. Another acoustic cardiographic metric is a surrogate for a myocardial performance index (MPI) that is based on at least a duration of heart sound S1 and a duration of heart sound S2.

Another example is directed to a device including, a heart sound sensor configured to obtain a heart sound signal, an electrogram (EGM) sensor configured to obtain an EGM signal, and a processor connected to the heart sound sensor and to the EGM sensor and configured to generate one or more acoustic cardiographic metrics based on at least one of the heart sound signal received from the heart sound sensor and the EGM signal received from the EGM sensor for a set of cardiac pacing parameters. The acoustic cardiographic metrics include one or more of: an indication of atrioventricular (AV) dyssynchrony based on at least an interval from heart sound S2 to heart sound S1; an indication of interventricular (VV) dyssynchrony based on a splitting of at least one of heart sound S1 and heart sound S2; an indication of Left interventricular dyssynchrony based on at least one of electromechanical activation delay (EMAT), aortic pre-ejection interval, heart sound M1 duration, and heart sound A2 duration; a surrogate for a myocardial performance index (MPI) based at least on a duration heart sound S1 and a duration of heart sound S2; an indication of left ventricle (LV) fill time based on the interval between heart sound S2 and heart sound S1; and an indication of LV contractility based on at least one of: the ratio of EMAT plus heart sound S1 duration divided by the interval between heart sound S1 and heart sound S2, the interval between S1 and S2, or the ratio of EMAT plus S1 duration divided by an R to R interval of the EGM.

Various examples are directed to an implantable device with CRT optimization capabilities. The implantable device includes sensors to collect both heart sounds and EGM signals. Based on the signals, a CRT optimization protocol may be implemented in a closed-loop, adaptive, and ambulatory fashion. The optimization may occur periodically or upon satisfaction of a certain condition. The condition may be patient activity based, such as low or no patient activity, or it may be acoustic cardiographic metric based, where a particular metric is observed to be outside a predetermined range. The implantable device may initiate a CRT optimization protocol without a signal from an external device, and may change CRT settings without receiving physician input.

The details of one or more examples are set forth in the accompanying drawings and the description below. Other features, objects, and advantages will be apparent from the description and drawings, and from the claims.

DETAILED DESCRIPTION

Figure 1:
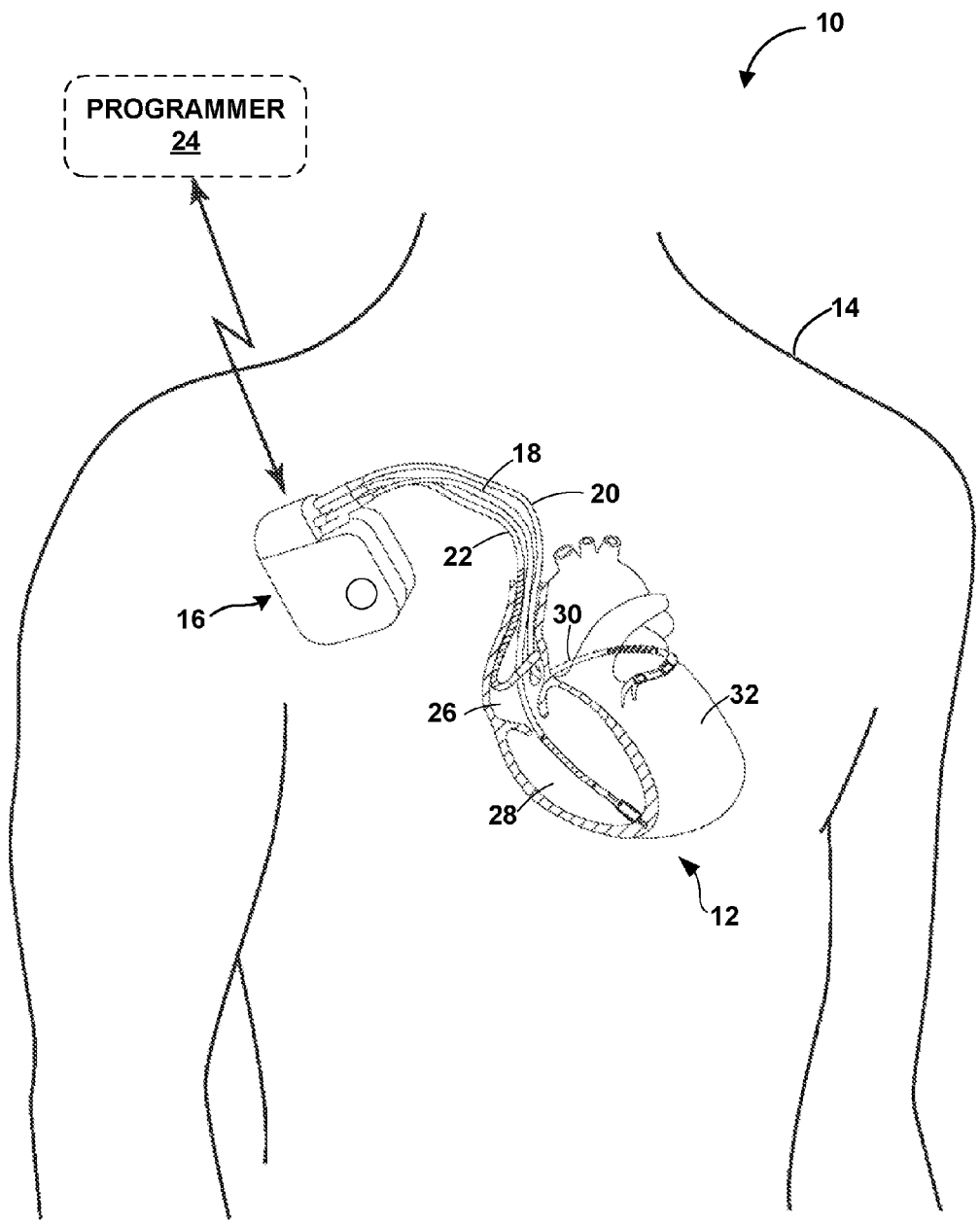
FIG. 1 is a conceptual diagram illustrating an example system that detects heart sounds and EGM signals for CRT optimization, consistent with an example of the present disclosure.

The techniques described in this disclosure may allow a medical device to detect heart sounds to aid in the optimization of CRT delivered by the medical device or by another medical device. The heart sounds are used in conjunction with EGM signals to provide information regarding the functioning of numerous aspects of the heart. The inclusion of a heart sound sensor within an IMD or in communication with the IMD, in combination with EGM signal monitor, allows for adaptive and/ambulatory optimization of the pacing parameters of the IMD. In various examples, the optimization of CRT may be performed automatically, without input from a physician or other clinician.

As used herein, the term heart sound refers to a feature of a heart sound signal, such as the S1, S2, S3, or S4 heart sounds. There may be multiple heart sounds, e.g., each of an S1, S2, S3 and S4 heart sound, for any given cardiac cycle or heart beat. In some examples, the medical device classifies a heart beat or cardiac cycle as normal or abnormal based on the classifications for one or more heart sounds detected during the heart beat or cardiac cycle. In such examples, the medical device may confirm that a cardiac rhythm is treatable when one or more heart beats are classified as abnormal, or withhold therapy when one or more heart beats are classified as normal.

In general, heart sounds are associated with mechanical vibrations of a patient's heart and the flow of blood through the heart valves, and, thus, are highly correlated with pressure gradients across heart valves and blood pressure. Heart sounds are not only due to vibrations of and pressure within the heart, but may be due to the entire cardiohemic system, e.g., blood, heart, great arteries, etc. Heart sounds recur with each cardiac cycle and are separated and classified according to the activity associated with the vibration. The first heart sound is referred to as "S1," and can be thought of as the vibration sound made by the heart during closure of the atrioventricular (AV) valves, i.e., the mitral valve and tricuspid valve. The S1 sound can sometimes be broken down into the M1 sound, from the closing of the mitral valve, and the T1 sound, from the closing of the tricuspid valve.

The second heart sound is referred to as "S2," and results from the closure of the semilunar valves, i.e., the pulmonary and aortic valves. The S2 heart sound can be thought of as marking the beginning of diastole. The S2 sound can also be broken down into component parts. The P2 sound is from the closing of the pulmonary valve and the A2 sound is from the closing of the aortic valve. The third and fourth heart sounds are referred to as "S3" and "S4," respectively, and can be conceptualized as related to filling of the ventricles during diastole. S3 is due to rapid filling of the ventricles and can occur when the ventricular wall is not relaxed when a large volume of blood flows into the ventricle from the atria. S4 is caused by blood rapidly filling into the ventricles from the atria due to atrial contraction.

Heart sounds provide important information about the mechanical function of the heart. For instance, an increase in the amplitude of the S3 sound is associated with worsening heart failure with elevated left ventricle (LV) filling pressure. The S4 sound is caused by atrial contraction when the left ventricle loses its compliance due to, for example, acute myocardial infarction and ischemia. The amplitude of S1 heart sound has been shown to correlate with the maximum rate of rise of left ventricular pressure (LV dP/dt Max), which is a measure of cardiac contractility. The interval between Q-wave (or R-wave) from EGM and S1 heart sound represents both the delay for electrical activation of the ventricle as well as mechanical delay to close the mitral and tricuspid valves. This is often referenced to as electromechanical activation delay (EMAT). The shortening of the interval has been predictive of response to CRT. The interval from S1 to S2 sounds represents ejection time (ET) which is correlated with stroke volume and cardiac output.

Heart sounds can be used to approximately provide a mechanical function assessment for the heart similar to echocardiography (Echo) without the need for a patient to travel to a doctor's office and without the need for additional equipment. For example, Echo analysis uses left-ventricular diastolic filling time, collided E and A waves, and mitral valve incompetence with late diastolic regurgitation to asses AV dyssynchrony. Correspondingly, heart sound-based analysis can approximately use the interval from the S2 to S1 sound, the interval from the S2 to S4 sound, the interval from the S4 to S1 sound and the S1 acceleration time to assess AV dyssynchrony. Echo analysis uses the difference between aortic and pulmonary pre-ejection times (i.e., the interval from the start of pulmonary flow to the beginning of aortic flow) to assess interventricular (VV) dyssynchrony.

Heart sound-based analysis can be used to assess VV dyssynchrony using the splitting time between M1 and T1 in S1 and/or the splitting time between A2 and P2 in S2. Echo analysis may use the aortic pre-ejection interval, time to isovolumic contraction and septal-to-posterior wall motion delay to assess left intraventricular dyssynchrony. Heart sound-based analysis can approximately use EMAT plus S1 duration, EMAT, and M1 duration or A2 duration to assess left intraventricular dyssynchrony. Echo analysis uses myocardial performance index (MPI) (i.e., the ratio of (ICT+IRT)/ET, where ICT=isovolumic contraction time, IRT=isovolumic relaxation time, and ET=ejection time) to assess both systolic and diastolic function. Heart sound-based analysis can approximately use the ratio of (S1 duration+S2 duration)/(interval between S1 and S2) as a surrogate for MPI.

The approximations for Echo-based metrics for assessing various function of the heart may be done automatically inside an IMD by processing heart sounds and EGM signals. Heart sound and EGM signals contain specific information regarding electrical, mechanical, contractility, and left ventricle filling functions of the patient's heart. Accordingly, combinations of heart sound and EGM signals may be used to provide an ambulatory, adaptive, patient-specific optimization scheme that may be implemented inside the IMD. Such a system may be used to support individualized CRT, where therapy is tailored to an individual patient's needs.

A heart sound sensor, such as a piezoelectric sensor or other acoustic sensor, may be implemented with an implantable medical device (IMD), e.g., on a lead or within a housing of the IMD. Enclosing the sensor within the housing of the IMD may provide additional protection for the sensor. Alternatively, the heart sound sensor may be implanted separately from the IMD and include a telemetry module allowing for wireless communication between the heart sound sensor and the IMD.

Various examples of the present disclosure may be used to obtain physiologically relevant information to suggest optimal pacing sites, i.e., choosing between a number of electrodes and electrode combinations. For instance, acoustic cardiographic metrics derived from heart sounds and EGM may be used to decide which modality to implement between left ventricle (LV) pacing (or "fusion pacing"), right ventricular (RV) pacing or biventricular (BiV) pacing. In examples where a multi-polar lead, such as a quadripolar lead, is used, the physiological information may be used to decide which electrode to use for LV pacing or which vector to use for pacing RV and LV. In other words, this information may be used to select a particular electrode combination for delivery of pacing therapy.

Physiologically relevant information derived from heart sounds may be used to help set a "fusion band" (i.e., the BiV pacing window) for "fusion pacing" or to fine-tune other EGM-based adaptive algorithms. Electrical fusion between LV pacing and spontaneous RV activation is considered helpful for resynchronization in sinus rhythm patients treated with single site LV pacing. The "fusion band" is defined as the range of AV intervals within which a surface electrocardiogram (ECG) shows an intermediate morphology (transition) of the QRS from a primarily left-sided pacing (Right bundle branch blocking, "RBBB", type) to primarily right-sided paced (Left BBB type) morphology. Pacing from the left ventricle creates normal sequence splitting of S1 (M1 then T1) due to delayed contraction in the right ventricle. In a similar manner, pacing from the right ventricles may create reverse splitting of S1 (T1 then M1) due to delay in LV contraction and a change in the pressure gradient across the valves. Accordingly, by checking the S1 splitting time under different AV delay settings, the fusion band and the optimal AV delay setting for a specific patient can be defined. Based on the information obtained from the heart sounds and EGM signals, an AV delay may be set inside the fusion band that may support the persistence of fusion and the associated hemodynamic benefits, even during continuous variation of spontaneous AV conduction and in particular during physical exercise.

In various examples, physiologically relevant information obtained from detected heart sounds and EGM may be used to suggest optimal pacing timing. For instance, the optimal AV delay for dual-chamber pacing devices, or sensed and pacing AV and VV delays in triple chamber pacing devices. Certain examples may also include monitoring and/or use of rate-responsive parameters. The information may also be used to determine parameters for heart rate-adaptive AV delay and for adaptive CRT. Further, the physiologically relevant information may be used to optimize pacing parameter settings at different heart rates (e.g., forcing rate via pacing or simulating exercise). For example, S2 detection may be monitored to assure that a pacing stimulation was not applied until a period of time after cardiac relaxation began, as indicated by S1, to avoid impairment of diastolic function. The use of S2 detection to monitor pacing application can also reduce the risk for reduced diastolic cardiac perfusion. Various heart sounds and EGM signal features can also be used to measure the filling interval of the ventricle to avoid pacing rates that would inappropriately restrict filling.

In various examples, optimal pacing parameters may be derived from a single determination of a plurality of acoustic cardiographic metrics. Alternatively, optimal pacing parameters may be derived in an iterative fashion where different acoustic cardiographic metrics are determined at different values of the parameter and then cross-compared to find the optimal setting for the parameter. In other examples the acoustic cardiographic metrics are cross-compared to find an optimal setting. Alternatively, or in addition, multi-variable integration models, such as probability-correlation based, neural network based, fuzzy-logic based, Bayesian network based, or rule-based models, may be used to combine all of the different acoustic cardiographic metrics together into one index for search for the optimal pacing parameter setting for an individual patient.

The various examples described in this disclosure may be implemented to allow for ambulatory monitoring of a patient's cardiac function and health. The various examples may also be used to automatically provide changes to various therapies provided by an IMD to a patient without feedback from a physician or other clinician. The CRT optimization may allow for heart failure monitoring and management with fewer visits to a physician and therapy that is more responsive to changes of a patient's condition.

FIG. 1 is a conceptual diagram illustrating an exemplary system 10 that detects heart sounds and electrogram (EGM) signals to be used to optimize CRT therapy provided to patient 14. In particular, system 10 provides cardiac pacing according to a set of pacing parameters. The pacing parameters may include, for example, AV delay, VV delay, electrode selection, lead placement, pacing site selection, pacing vector configuration, frequency of stimulation, or strength of stimulation. The detected heart sounds and EGM signals may be used to assess the efficacy of the pacing parameters. In some examples, acoustic cardiographic metrics are derived from the heart sound and EGM signals. The values of one or more acoustic cardiographic metrics may be compared to either a threshold or a predetermined, e.g., previously saved, value. If system 10 determines the acoustic cardiographic metric is above (or below) a threshold, or outside a predetermined range surrounding the saved value, an optimization procedure may be implemented. In other examples, the system 10 can initiate an optimization procedure based on a predetermined time interval or in response to an external command.

System 10 includes implantable medical device (IMD) 16, which is connected to leads 18, 20, and 22 and is optionally communicatively coupled to a programmer 24. IMD 16 senses electrical signals attendant to the depolarization and repolarization of heart 12, e.g., a cardiac EGM, via electrodes on one or more leads 18, 20 and 22 or the housing of IMD 16. IMD 16 also delivers therapy in the form of electrical signals to heart 12 via electrodes located on one or more leads 18, 20 and 22 or a housing of IMD 16. The therapy may be pacing, cardioversion and/or defibrillation pulses. IMD 16 also includes, or is coupled via one or more leads 18, 20 and 22 to, one or more heart sound sensors (not shown in FIG. 1). The heart sound sensor may be in the IMD housing, on one or more of leads 18, 20 and 22, on an additional lead (not shown), or in a separate device, for example. IMD may similarly include or be coupled to other sensors, such as one or more accelerometers, for detecting other physiological parameters of patient 14, such as activity or posture.

In some examples, programmer 24 takes the form of a handheld computing device, computer workstation or networked computing device that includes a user interface for presenting information to and receiving input from a user. A user, such as a physician, technician, surgeon, electro-physiologist, or other clinician, may interact with programmer 24 to retrieve physiological or diagnostic information from IMD 16. A user may also interact with programmer 24 to program IMD 16, e.g., select values for operational parameters of the IMD. In certain examples various functions of the programmer 24 may be automated. For example, the operational parameters may be selected automatically in response to one or more acoustic cardiographic metrics. In other examples the function of programmer 24 may be split between an external programmer and an internal programmer within IMD 16.

IMD 16 and programmer 24 may communicate via wireless communication using any techniques known in the art. Examples of communication techniques may include, for example, low frequency or radiofrequency (RF) telemetry. Other techniques are also contemplated. In some examples, programmer 24 may include a programming head that may be placed proximately to the patient's body near the IMD 16 implant site in order to improve the quality or security of communication between IMD 16 and programmer 24. In other examples, programmer 24 may be located remotely from IMD 16, and communicate with IMD 16 via a network. In some examples, IMD 16 and programmer 24 may work with general network technology and functionality similar to that provided by the Medtronic CareLink® Network developed by Medtronic, Inc., of Minneapolis, Minn.

As will be described in greater detail, IMD 16 may deliver therapeutic stimulation of "therapy" to a patient 14 for cardiac rhythm management of heart 12 based, at least in part, on heart sounds. The timing, frequency, duration, location, and/or strength of the stimulation provided by leads, 18, 20 and/or 22 may be determined based on acoustic cardiographic metrics derived from heart sounds, alone or in combination with EGM signals.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

Techniques for optimizing CRT based on heart sounds and EGM signals are primarily described herein as being performed by IMD 16, e.g., by a processor of IMD 16. In other examples, some or all of the functions ascribed to IMD 16 or a processor thereof may be performed by one or more other devices, such as programmer 24, or a processor thereof. For example, IMD 16 may process heart sounds and/or EGM signals to determine whether a therapy should continue to be delivered based on current pacing parameters or whether adjustments to the parameters should be made, and automatically control the pacing parameters used by IMD 16 to deliver the therapy.

Alternatively, programmer 24 may process heart sound and/or EGM signals received from IMD 16 to determine whether a therapy should continue to be delivered based on current pacing parameters or whether adjustments to the parameters should be made, and control under what pacing parameters IMD 16 delivers the therapy. Furthermore, although described herein with respect to an IMD, in other examples, the techniques described herein may be performed or implemented in an external medical device, which may be coupled to a patient via percutaneous or transcutaneous leads.

For the various examples described with respect to FIG. 1, IMD 16 may use the information obtained from processing detected heart sounds and/or EGM signals to automatically evaluate the effectiveness of the therapy parameters being applied. In response to the evaluation, the IMD 16 may automatically adjust therapy, e.g., by adjusting the selected electrode combination and or other pacing parameters such as AV delay, VV delay, frequency of stimulation, and strength of stimulation. In some examples, IMD 16 stores information for evaluation by the physician. In other examples, the IMD 16 may provide the physician with recommended adjustments to the therapy. In various examples, the adjustments to the pacing parameters may include adjustment to the pacing provided to the left ventricle, to the right ventricle, or to both ventricles. In other examples, the electrode combinations may be adjusted for one or both chambers.

Figure 2:
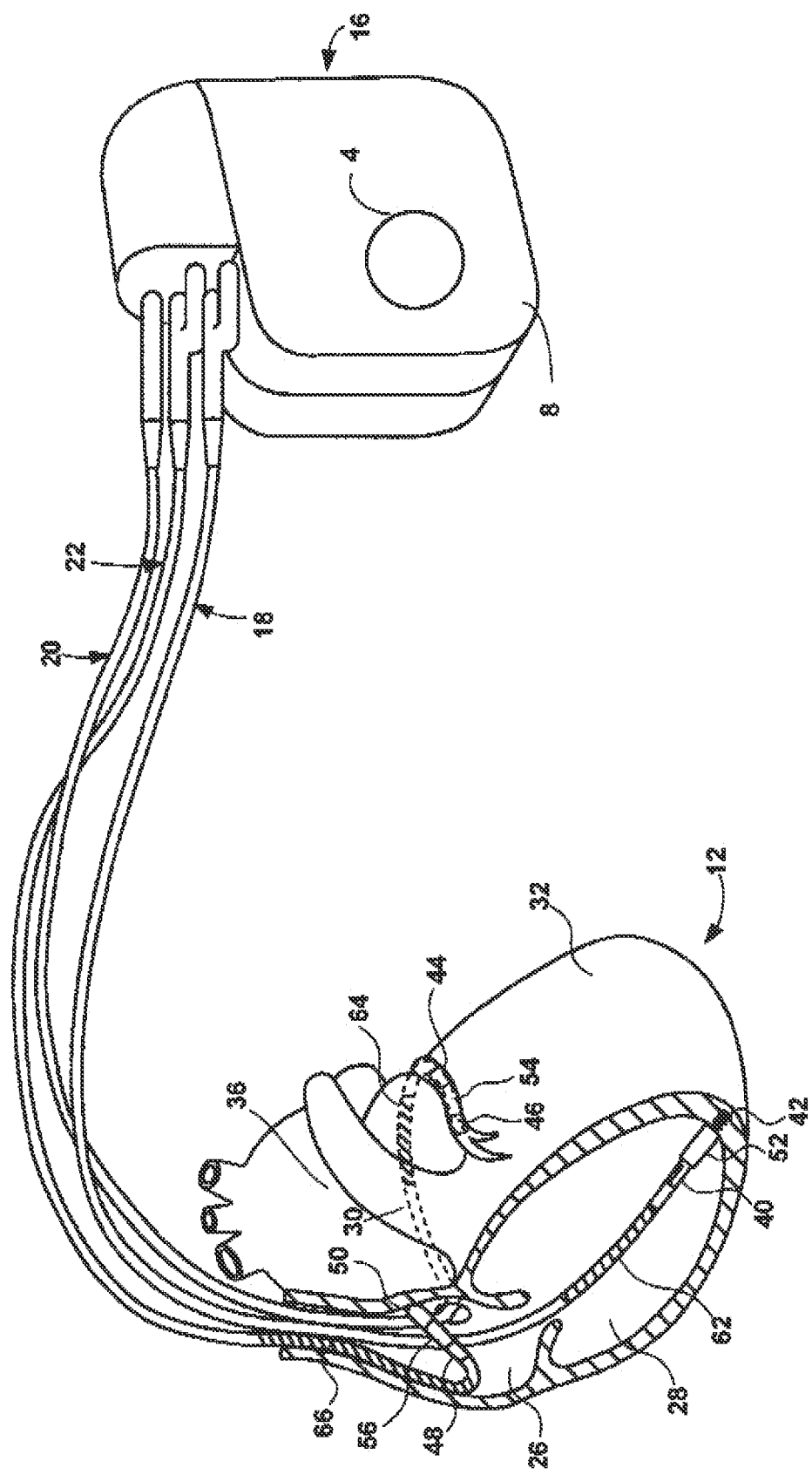
FIG. 2 is a conceptual diagram illustrating the implantable medical device (IMD) and leads of the system shown in FIG. 1 in greater detail.

FIG. 2 is a conceptual diagram illustrating IMD 16 and leads 18, 20 and 22 of system 10 in greater detail. In the illustrated example, bipolar electrodes 40 and 42 are located adjacent to a distal end of lead 18. In addition, bipolar electrodes 44 and 46 are located adjacent to a distal end of lead 20, and bipolar electrodes 48 and 50 are located adjacent to a distal end of lead 22. In alternative examples, not shown in FIG. 2, one or more of leads 18, 20 and 22 may include quadrapole electrodes located adjacent to a distal end of the lead.

In the illustrated example, electrodes 40, 44 and 48 take the form of ring electrodes, and electrodes 42, 46 and 50 may take the form of extendable helix tip electrodes mounted retractably within insulative electrode heads 52, 54 and 56, respectively. Leads 18, 20, 22 also include elongated electrodes 62, 64, 66, respectively, which may take the form of a coil. In some examples, each of electrodes, 40, 42, 44, 46, 48, 50, 62, 64 and 66 is electrically coupled to a respective conductor within the lead body if its associated lead 18, 20, 22 and thereby coupled to circuitry within IMD 16.

In some examples, IMD 16 includes one or more housing electrodes, such as housing electrode 4 illustrated in FIG. 2, which may be formed integrally with an outer surface of hermetically-sealed housing 8 of IMD 16 or otherwise coupled to housing 8. In some examples, housing electrode 4 is defined by an uninsulated portion of an outward facing portion of housing 8 of IMD 16. Other divisions between insulated and uninsulated portions of housing 8 may be employed to define two or more housing electrodes. In some examples, a housing electrode comprises substantially all of housing 8. Pacing may be delivered to heart 12 via a various combination of the electrodes (pacing vectors) described above. As described in more detail as follows, pacing vectors may include unipolar, bipolar, or multipolar vectors. In some examples, heart sound and EGM based information may be used to select combinations to provide efficacious pacing in terms of cardiac function.

As described in further detail with reference to FIG. 3, housing 8 encloses a signal generator that generates therapeutic stimulation, such as cardiac pacing, cardioverison and defibrillation pulses, as well as a sensing module for sensing electrical signals attendant to the depolarization and repolarization of heart 12. Housing 8 may also enclose a heart sound sensor that generates an electrical signal based on sensed heart sounds. The heart sound sensor may be enclosed within housing 8. Alternatively, the heart sound sensor may be integrally formed with or carried on an outer surface of housing 8, carried on or within a lead coupled to IMD 16, such as one or more leads 18, 20 and 22, or be a separate, remote sensor that wirelessly communicates with IMD 16, programmer 24 or any other device described herein.

IMD 16 senses electrical signals attendant to the depolarization and repolarization of heart 12 via electrodes 4, 40, 42, 44, 46, 48, 50, 62, 64 and 66. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 4.

In some examples, IMD 16 delivers pacing pulses via bipolar combinations chosen based on heart sounds and/or EGM signals as analyzed by a cardiac signal analyzer. For example, bipolar combinations of electrodes 40, 42, 44, 46, 48, and 50 are used to produce depolarization of cardiac tissue of heart 12. In some examples, IMD 16 delivers pacing pulses via any of electrodes 40, 42, 44, 46, 38 and 50 in combination with housing electrode 4 in a unipolar configuration. The particular electrodes delivering pulses may be determined based in part on a CRT optimization routine that uses heart sounds and/or EGM signals. In other examples, the choice of electrodes delivering pacing pulses may be based on default settings. Furthermore, IMD 16 may deliver cardioversion or defibrillation pulses to heart 12 via any combination of elongated electrodes 62, 64, 66 and housing electrode 4.

The illustrated numbers and configurations of leads 18, 20 and 22 and electrodes are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to intracardiac leads 18, 20 and 22, system 10 may include one or more epicardial or subcutaneous leads not positioned within the heart. As another example, system 10 may include an additional lead that carries a heart sound sensor positioned such that signals generated by the heart sound sensor include heart sounds.

Figure 3:
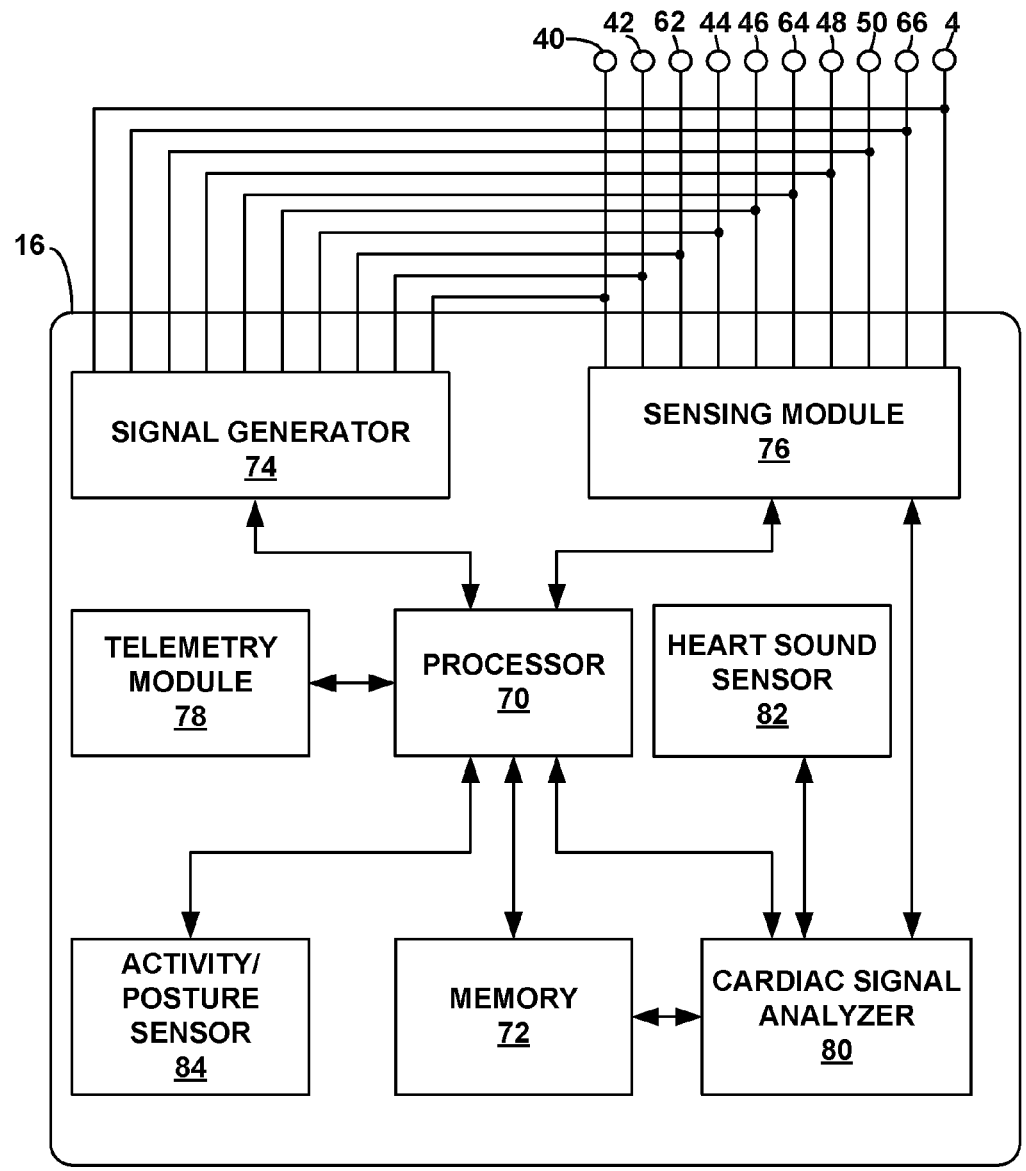
FIG. 3 is a block diagram illustrating an exemplary configuration of the IMD of FIG. 1.

FIG. 3 is a block diagram illustrating an example configuration of IMD 16. In the illustrated example, IMD 16 includes a processor 70, memory 72, signal generator 74, sensing module 76, telemetry module 78, cardiac signal analyzer 80, heart sound sensor 82 and activity and/or posture sensor 84. Memory 72 includes computer-readable instructions that, when executed by processor 70, cause IMD 16 and processor 70 to perform various functions attributed to IMD 16 and processor 70 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof. Generally, processor 70 controls signal generator 74 to deliver stimulation therapy to hear 12 of patient 14 according to a selected one or more of therapy programs or parameters, which may be stored in memory 72. As an example, processor 70 may control signal generator 74 to deliver electrical pulses with the amplitudes, pulse widths, frequency, or electrode polarities specified by the selected one or more therapy programs. The therapy programs may be selected by the processor 70 based on information from the cardiac signal analyzer 80.

Signal generator 74 is configured to generate and deliver electrical stimulation therapy to patient 12. As shown in FIG. 3, signal generator 74 is electrically coupled to electrodes 4, 40, 42, 44, 46, 48, 50, 62, 64 and 66, e.g., via conductors of the respective leads 18, 20, and 22 and, in the case of housing electrode 4, within housing 8. For example, signal generator 74 may deliver pacing pulses, defibrillation shocks or cardioversion shocks to heart 12 via at least two of electrodes 4, 40, 442, 44, 46, 48, 50, 62, 64 and 66. In other examples, signal generator 74 delivers stimulation in the form of signals other than pulses such as sine waves, square waves, or other substantially continuous time signals.

Signal generator 74 may include a switch module (not shown) and processor 70 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 76 monitors electrical cardiac signals from any combination of electrodes 4, 40, 42, 44, 46 48, 50, 62, 64, and 66. Sensing module 76 may also include a switch module which processor 70 controls to select which of the available electrodes are used to sense the heart activity, depending upon which electrode combination is used in the current sensing configuration.

Sensing module 76 may include one or more detection channels, each of which may comprise an amplifier. The detection channels may be used to sense the cardiac signals. Some detection channels may detect events, such as R-waves or P-waves, and provide indications of the occurrences of such events to processor 70 and/or cardiac signal analyzer 80. One or more other detection channels may provide the signals to an analog-to-digital converter, for conversion into a digital signal for processing or analysis by processor 70 or cardiac signal analyzer 80.

For example, sensing module 76 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 70 then uses that detection in measuring frequencies of the sensed events. Cardiac signal analyzer 80 may use the detection in connection with sensed heart sounds to determine one or more acoustic cardiographic metrics.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

In some examples, sensing module 76 includes a wide band channel which may comprise an amplifier with a relatively wider pass band than the narrow band channels. Signals from the electrodes that are selected for coupling to the wide-band amplifier may be converted to multi-bit digital signals by an analog-to-digital converter (ADC) provided by, for example, sensing module 76, processor 70, or cardiac signal analyzer 80. Processor 70 may analyze the digitized version of signals from the wide band channel. Processor 70 may employ digital signal analysis techniques to characterize the digitized signals from the wide band channel to, for example, detect and classify the patient's heart rhythms. In other examples, the cardiac signal analyzer 80 employs digital signal analysis techniques to characterize the digitized signals from the wide band channel. The digitized signals may be used in conjunction with heart signals to produce an acoustic cardiographic metric.

Processor 70 may detect and classify the patient's heart rhythm based on the cardiac electrical signals sensed by sensing module 76 employing any of the numerous signal processing methodologies known in the art. In certain examples, processor 70 may provide the processed signal to cardiac signal analyzer 80 for further processing or combination with heart sound signals. In other examples, sensing module 76 provides the cardiac electrical signals sensed directly to cardiac signal analyzer 80. In some examples, sensing module 76 provides the sensed cardiac electrical signals to both processor 70 and cardiac signal analyzer 80 for different signal processing. In various examples, processor 70 may maintain escape interval counters that may reset upon sensing of R-waves by sensing modules 76. The value of the count present in the escape interval counters when reset by sensed depolarizations may be used by processor 70 to measure the durations of R-R intervals, which are measurement that may be stored in memory 72 and may be used by cardiac signal analyzer 80. Processor 70 may use the count in the interval counters to detect a tachyarrhythmia, such as ventricular fibrillation or ventricular tachycardia. A portion of memory 72 may be configured as a plurality of recirculating buffers, capable of holding a series of measured intervals, which may be analyzed by processor 70 to determine whether the patient's heart 12 is presently exhibiting atrial or ventricular tachyarrhythmia.

In the example of FIG. 3, e.g., to aid in CRT optimization, IMD 16 also includes heart sound sensor 82 and cardiac signal analyzer 80. Heart sound sensor 82 generates an electrical signal based on sensed heart sounds of patient 14, and may be implemented as a piezoelectric sensor, a microphone, an accelerometer, or other type of acoustic sensor. In some examples, heart sound sensor 82 may comprise more than one sensor. For example, heart sound sensor 82 may include multiple individual sensors. For example, the heart sounds sensor may include multiple accelerometers, microphones or piezoelectric devices. In some examples, the heart sensor may be used as both an acoustic to electrical transducer and as an electrical to acoustic transducer. In such examples, the sensor may also be used to generate an audible alarm for the patient, such as a buzzing or beeping noise. The alarm may be in response to an acoustic cardiographic metric passing a predefined threshold.

In the illustrated example of FIG. 3, heart sound sensor 82 is enclosed within housing 8 of IMD 16. In some examples, heart sound sensor 82 may be formed integrally with or on an outer surface of housing 8. In other examples, heart sound sensor 82 is located on a lead that is coupled to IMD 16 or may be implemented in a remote sensor that wirelessly communicates with IMD 16. In any case, heart sound sensor 82 is electrically or wirelessly coupled to circuitry contained within housing 8 of IMD 16.

Cardiac signal analyzer 80 receives the electrical signal generated by heart sound sensor 82. In one example, cardiac signal analyzer 80 may process the sensor signal generated by heart sound sensor 82 to detect heart sounds, classifies the detected heart sounds as either normal or abnormal, and generates one or more acoustic cardiographic metrics indicative of heart performance based on the classification of one or more of the detected heart sounds. In some examples, cardiac signal analyzer 80 processes the heart sensor signal to generate an envelope signal, applies an algorithm that uses an adaptively decaying threshold to detect heart sounds within the envelope signal, extracts heart sound features from the detected heart sounds, and classifies the detected heart sounds based on the heart sound features. In some examples, the detected heart sound features may be compared to values for each feature stored in memory 72. The heart sounds may then be classified based on deviation from the stored values. The heart sound features and their classifications may be used to determine an acoustic cardiographic metric.

In some examples the classified heart sounds are used by the cardiac signal analyzer 80 along with EGM information received from an EGM signal collected by the sensing module 76. In some examples, the EGM information may be extracted by the sensing module 76, and provided to processor 70. The EGM information may then be provided to the cardiac signal analyzer 80 by memory 72 or processor 70. In some examples, the unprocessed signal is provided to processor 70 by sensing module 76 for information extraction. In other examples, the EGM information may also be extracted from the EGM signal by the cardiac signal analyzer 80. Examples of the operation of cardiac signal analyzer 80 in accordance with these exemplary methods are described in greater detail with respect to FIGS. 4-8. A heart sound-based indication may be output to processor 70. In other examples, an acoustic cardiographic metric is output to the processor 70. The processor may initiate a CRT optimization routine based on the information or, during a CRT optimization routine, determine a new set of pacing parameters to be implemented.

The acoustic cardiographic metrics may include information regarding the functioning of various aspects of the heart. For example, an increase in the amplitude of the S3 sound is associated with worsening heart failure with elevated left ventricle (LV) filling pressure. The S4 sound is caused by atrial contraction when the left ventricle loses its compliance due to, for example, acute myocardial infarction and ischemia. The amplitude of the S1 heart sound has been shown to correlate with the maximum rate of rise of left ventricular pressure (LV dP/dt Max), which is a measure of cardiac contractility. The interval between the Q-wave (or R-wave) from the EGM and the S1 heart sound represents both the delay for electrical activation of the ventricle as well as mechanical delay to close the mitral and tricuspid valves. This delay is often referred to as electromechanical activation time (EMAT). The shortening of the interval between the Q-wave (or R-wave) from the EGM and the S1 heart sound has been found to be predictive of patient response to CRT. The interval between the S1 and S2 sounds represents the ejection time (ET), which is correlated with stroke volume and cardiac output.

The acoustic cardiographic metrics based on various heart sounds may also be analyzed by processor 70 to assess the mechanical function of the heart in a manner similar to that provided by an external Echo machine. For example, Echo analysis uses left-ventricular diastolic filling time, collided E and A waves, and mitral valve incompetence with late diastolic regurgitation to asses AV dyssynchrony. Heart sound-based analysis may be performed by cardiac signal analyzer 80 or processor 70 to provide approximates of the Echo analysis. For example heart sound-based analysis may, correspondingly, approximately use the interval from the S2 to S1 sound, the interval from the S2 to S4 sound, and the interval from the S4 to S1 sound and S1 acceleration time to assess AV dyssynchrony.

Echo analysis uses the difference between aortic and pulmonary pre-ejection times (i.e., the interval from the start of pulmonary flow to the beginning of aortic flow) to assess interventricular (VV) dyssynchrony. Heart sound-based analysis can be used to assess VV dyssynchrony using the splitting time between M1 and T1 in S1 and/or the splitting time between A2 and P2 in S2. Echo analysis may use aortic pre-ejection interval, time to isovolumic contraction and septal-to-posterior wall motion delay to assess left intraventricular dyssynchrony. Heart sound-based analysis can approximately use EMAT plus S1 duration, EMAT, and M1 duration or A2 duration to assess left intraventricular dyssynchrony. Echo analysis uses myocardial performance index (MPI) (i.e., the ratio of (ICT+IRT)/ET, where ICT=isovolumic contraction time, IRT=isovolumic relaxation time, and ET=ejection time) to assess both systolic and diastolic function. Heart sound-based analysis can approximately use the ratio of (S1 duration+S2 duration)/(interval between S1 and S2) as a surrogate for MPI.

In some examples, IMD 16 analyzes the heart sound and EGM signals prior to determining an initial set of pacing parameters for delivery of therapy to the heart of the patient. In other examples, IMD 16 analyzes heart sounds and EGM signals during delivery of pacing pulses based on a preselected set of pacing parameters. For example, IMD 16 may classify the cardiac rhythm as within an acceptable range, or if outside the range, initiate a CRT optimization routine to adjust the pacing parameters to drive the cardiac rhythm into the acceptable range. In another example, IMD 16 may change to a different, previously determined, set of pacing parameters based on the classification of the cardiac rhythm.

Signal generator 74 may deliver the pacing pulses based on a set of pacing parameters. Cardiac signal analyzer 80 may then process the heart sound signal received from heart sound sensor 82 during the pacing to determine if the pacing results in heart sounds that indicate that one or more measures of cardiac function are within an acceptable range. Cardiac signal analyzer 80 determines whether to modify the set of pacing parameters applied to the heart using a CRT optimization routine based on the analysis. During a CRT optimization routine, the cardiac signal analyzer 80 may store heart sound and EGM signal information regarding at least one acoustic cardiographic metric for each of a plurality of sets of pacing parameters. At the end of the optimization routine, the set of pacing parameters with the best overall heart performance, e.g., in terms of one or more acoustic cardiographic metrics indicated by the heart sounds and EGM information, may be selected. The operation of cardiac signal analyzer 90 in accordance with this additional or alternative example is described in greater details with respect to FIG. 4.

Although processor 70 and cardiac signal analyzer 80 are illustrated as separate modules in FIG. 3, processor 70 and cardiac signal analyzer 80 may be incorporated in a single processing unit. Cardiac signal analyzer 80, and any of its components discussed in greater details below, may be a component of or a module executed by processor 70.

Furthermore, the components of and functionality provided by cardiac signal analyzer 80 are described herein with respect to examples in which cardiac signal analyzer 80 is located within IMD 16. However, it is understood that any one or more cardiac signal analyzers 80 may be individually or collectively provided by any one or more devices, such as IMD 16 and programmer 24, to individually or collectively provide the functionality described herein. Programmer 24 may receive electrical signals generated by heart sound sensor 82 from IMD 16 in examples in which programmer 24 includes a heart sound analyzer or a cardiac signal analyzer.

As illustrated in FIG. 3, IMD 16 may also include an activity and/or posture sensor 84. Activity and or posture sensor 84 may, for example, take the form of one or more accelerometers, or any other sensor known in the art for detecting activity, e.g., body movements or footfalls, or posture. In some examples, activity and/or posture sensor 84 may comprise a three-axis accelerometer. In some examples, heart sound sensor 82 and activity and/or posture sensor 84 may comprise one or more common accelerometers. As will be described in greater detail below with reference to FIGS. 5-8, processor 70 or cardiac signal analyzer 80 may use signals from activity and/or posture sensor 84 in various aspects of the heart sound and EGM signal analysis.

Telemetry module 78 includes any suitable hardware, firmware, software or any combination thereof for communicating with another device, such as programmer 24(FIG. 1). Under the control of processor 70, telemetry module 78 may receive downlink telemetry from and send uplink telemetry to programmer 24 with the aid of an antenna, which may be internal and/or external. In some examples, processor 70 may transmit cardiac signals, e.g., ECG or EGM signals, produced by sensing module 76 and/or signals by heart sound sensor 82 to programmer 24. Processor 70 may also generate and store marker codes indicative of different cardiac events output from sensing module 76 or cardiac signal analyzer 80, and transmit the marker codes to programmer 24. An example IMD with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety. Information which processor 70 may transmit to programmer 24 via telemetry module 78 may also include an indication of a change in disease state of the heart, an indication of a change in heart response to the therapy provided or an indication that the heart continues to response in the same (or similar) manner to the therapy provided, or the indications based on heart sounds and/or EGM signals. Such information may be included as part of a marker channel with an EGM.

Figure 4:
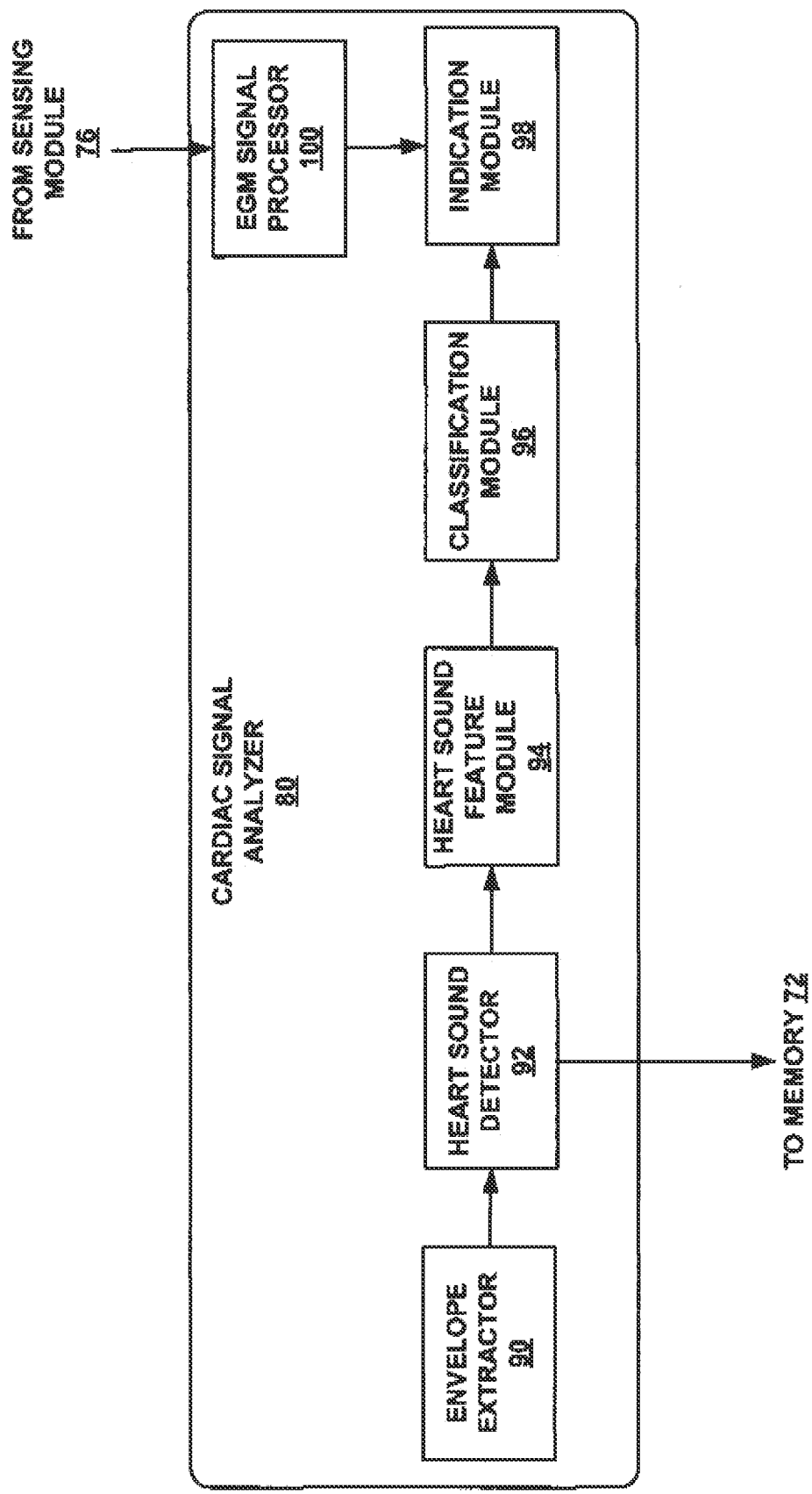
FIG. 4 is a block diagram illustrating an exemplary configuration of the cardiac signal analyzer shown in FIG. 3.

FIG. 4 is a block diagram illustrating an exemplary configuration of cardiac signal analyzer 80. As illustrated in FIG. 4, cardiac signal analyzer 80 may include an envelope extractor 90, heart sound detector 92, heart sound feature module 94, classification module 96, indication module 98, and EGM signal processor 100.

Envelope extractor 90 receives an electrical signal from heart sound sensor 82. The electrical signal may be digitized and parsed into segments of predetermined length. As an example, the electrical signal generated by cardiac signal analyzer 80 may be sampled at 256 Hertz (Hz) rate and parsed into segments including 100 or more sample points. Generally, envelope extractor 90 processes the received signal to extract an envelope, i.e., generate an envelope signal from the received signal. The envelope signal generally tracks the peaks of the received signal.

In some examples, envelope extractor 90 band pass filters, rectifies, and smoothes the sensor signal before extracting the envelope signal. For example, envelope extractor 90 may include a high pass filter, e.g., a 40 Hz high pass filter, and a low pass filter, such as a 70 Hz low pass filter, to remove unwanted signal components from the heart sound sensor signal. In some examples, a first order infinite impulse response (IIR) high pass filter with a cutoff frequency of 40 Hz and a third order IIR low pass filter with a cutoff of 70 HZ may be used. In other examples, a band bass filter with a 20 Hz high pass filter and a 70 Hz low pass filter is used. In some examples, analog filtering of the heart sound sensor signal may additionally or alternatively be performed prior to digitization of the signal and receipt by envelope extractor 90. As discussed above, IMD 16 may include analog-to digital conversion circuitry.

Envelope extractor 90 may also, in some examples, include rectification circuitry and circuitry that sums the rectified signal with left-shifted and right-shifted rectified signals in order to smooth the rectified signal. In this manner, envelope extractor may approximately apply an analytic function transform to the signal for envelope extraction. In other examples, envelope extractor 90 may use other methods to generate the envelope signal, such as the normalized average Shannon Energy, true Hilbert transform, or rectifying the derivative of the signal followed by moving window integration of the rectified derivative. In such examples, envelope extractor 90 extracts or generates the envelope signal of the processed signal, i.e., the band pass filtered, rectified, and smoothed signal. Extraction of the envelope signal may further include application of a box-car filter, such as a 16 point box-car filter, to the band pass filtered, rectified, and smoothed signal. Envelope extractor 90 outputs the envelope signal to heart sound detector 92.

Heart sound detector 92 utilizes an algorithm to detect heart sounds within the envelope signal. Generally, heart sound detector 92 identifies the local maximums of the envelope signal. In order to identify the local maximums that correspond to heart sounds, heart sound detector 92 may utilize an adaptively decaying threshold. The adaptively decaying threshold may be determined based on the running average of detected heart sound amplitudes, the running average of the envelope signal amplitude, and the mean heart sound-to-heart sound interval. Heart sound detector 92 compares the envelope signal to the adaptively decaying threshold to identify the local maximums. Heart sound detector 92 may store markers, referred to as "heart sound markers," for the identified local maximums within memory 72 or provide the heart sound markers directly to heart sound feature module 94.

Heart sound feature module 94 extracts features of the detected heart sounds. Example heart sound features include the mean period ratio (MPR) and matching score (MS) for a detected heart sound. The MPR for a detected heart sound is the period of the detected heart sound divided by the mean period of one or more template heart sounds. For example, the MPR may be determined for hearts sounds S1-S4, based on a template including the average length of each heart sound in a normally functioning heart. The MS may be determined using template matching schemes that compare detected heart sounds to template heart sounds, such as a wavelet template matching scheme or a "bounded template" matching scheme. An example wavelet template matching scheme is disclosed in U.S. Pat. No. 6,393,316 issued to Jeff Gillberg. An example bounded template matching scheme is disclosed in US Publication No. 20100185109, entitled "A Blurred Template Approach for Arrhythmia Detection," by Xin Zhang, Mark Brown, Xusheng Zhang, and Jeff Gillberg.

In some examples, template heart sounds used for determining the MPR and MS may be example heart sounds that are loaded into heart sound feature module 94. In other examples, template heart sounds may be heart sounds that were measured during a baseline interval of the patient. That is, the template heart sounds may be obtained from patient 14 during an identified or predetermined time period during which the patient is known to have a normal or desired cardiac rhythm.

In some examples, heart sound feature module 94 may load different templates depending upon information from the activity/posture sensor 84. For example, in situations where the activity/posture sensor 84 indicates that the patient 14 is at rest the heart sounds may be compared to a different template than when the patient 14 is standing, and yet another template when the patient's activity level is above a threshold.

Heart sound feature module 94 may determine different attributes of each of the detected heart sounds, as well as relationships between each heart sound. For example, the heart sound feature module 95 may determine the duration of each of the heart sounds, and the intervals between each heart sound and the other heart sounds. Heart sound feature module 94 may also determine the acceleration time of each of the heart sounds or the amplitude of the each of the heart sounds.

Heart sound feature module 94 may use a heart sound marker from heart sound detector 92 to center a window, e.g., a 48 point or sample window, at a detected heart sound and use the resulting segment of samples to determine the MPR and MS. For example, heart sound feature module 94 may determine the period of the band-pass filtered signal segment and use it to determine the MPR, and may compare the extracted envelope signal segment to a stored template to determine the MS. Heart sound feature module 94 may then provide the MPR and MS to classification module 96.

Classification module 96 classifies each of the detected heart sounds as either normal or abnormal based on the corresponding heart sound feature values. Classification of the heart sounds as normal or abnormal may be based on whether the features, e.g., the MPR and MS values, are within a predetermined range, or above or below a predetermined threshold.

Indication module 98 receives the classification information for each of the detected heart sounds from classification module 96 and information extracted from the EGM signal by EGM signal processor 100 or by Processor 70. Indication module 98 generates an indication of an acoustic cardiographic metric based on the received information. Generally, indication module 98 may generate the indication based on one or more heart sounds or EGM features. As an example, indication module 98 may generate an indication regarding left ventricular filling time based on the interval between S2 and S1. In certain more specific examples, the indication may also include information regarding whether the filling time is within an acceptable range. For example, if the interval between S2 and S1 is greater than 40% of the EGM R to R interval, the indication may be that the heart has adequate left ventricular filling time. In other examples, the acceleration time of S1 may indicate mitral valve late diastolic regurgitation if the acceleration time is below a threshold. In still other examples, indication module 98 may determine whether the split between M1 and T1 falls below between 20 and 40 milliseconds (ms). If the split falls within the range the indication may be that the split is within the normal range, and if the split is greater than 40 ms, the indication may be that the split is abnormal or outside the desired range. In some examples, the indication module 98 may determine whether the split between A2 and P2 falls below 20 ms. If the split is shorter than 20 ms, the indication may be that the split is normal. However, if the split is longer than 20 ms, the A2 to P2 split may be indicated as abnormal. Split time between M1 and T1, and A2 and P2 may indicate the level of synchronicity between the contractions of the ventricles. In other examples, the indication module 98 provides an indication to processor 70 that includes information regarding certain heart features, such as the amplitudes and/or durations of heart sounds S1-S4.

Indication module 98 provides one or more indications to processor 70, which determines whether a CRT optimization routine should be initiated. During a CRT optimization routine indication module 98 provides one or more indicators either to processor 70 or to memory 72 for each set of pacing parameters. The processor 70 may, for example, compare S3 and S4 sound amplitude and/or durations to previously collected samples stored in memory 72, and based on the comparison modify pacing parameters to minimize the amplitude and/or duration of S3 and/or S4. In other examples, the indication module 98 only provides an indication to processor 70 when the indication has changed.

Indication module 98 may provide one or more acoustic cardiographic metric to processor 70. The acoustic cardiographic metric may be, for example, an indication of worsening heart failure or a variety of heart function problems. In some examples, the acoustic cardiographic metric is an indication of atrioventricular (AV) dyssynchrony. In other examples, the acoustic cardiographic metric is an indication of interventricular (VV) dyssynchrony. In some examples, the acoustic cardiographic metric is an indication of left intraventricular dyssynchrony. In other examples, the acoustic cardiographic metric is a surrogate for a myocardial performance index (MPI) based on an echocardiograph. In some examples, the acoustic cardiographic metric is an indication of left ventricle (LV) filling time. In other examples, the acoustic cardiographic metric is an indication of LV contractility. In some examples, the acoustic cardiographic metric is an indication of the presence of systemic or pulmonary hypertension.

Figure 5:
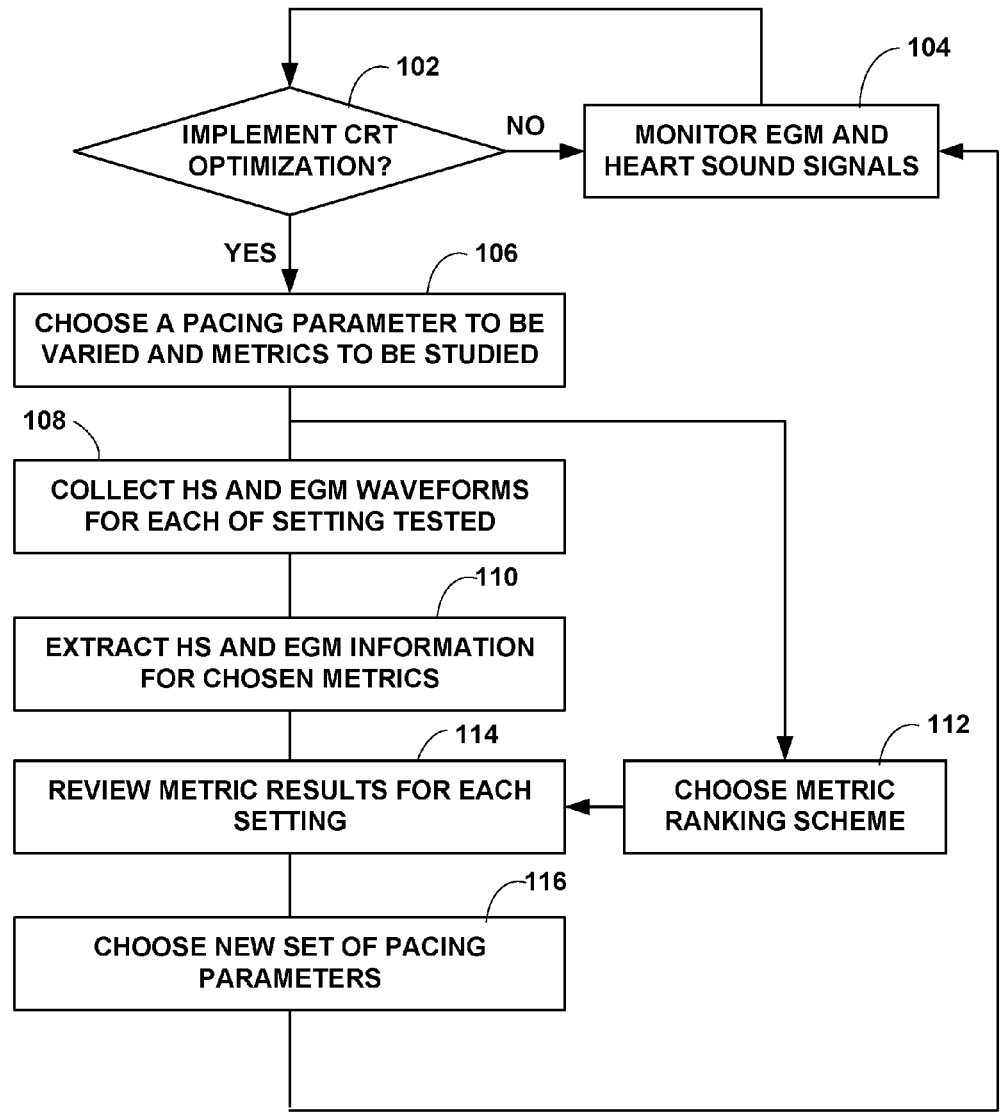
FIG. 5 is a flow chart illustrating an exemplary mode of operation for performing CRT optimization using heart sounds and EGM signals.

FIG. 5 is a flow chart illustrating an exemplary mode of operation for performing CRT optimization using heart sounds and EGM signals. The example method is described with respect to IMD 16 and its components shown in FIG. 3, but in other examples may be practiced, at least in part, by another device, such as programmer 24.

According to the illustrated example, processor 70 determines whether or not to implement CRT optimization (102). In one example, processor 70 may make the determination based on a time interval. The processor can implement the CRT optimization protocol once a day, once a week, once a month or once a year, for example. In other examples, CRT optimization may be applied on a substantially continuous or periodic basis. As another alternative, the decision may be based on data from the activity and posture sensor 84. For example, when a patient's activity level crosses a predetermined threshold, indicating that the patient is exercising, a CRT optimization scheme may be initiated to provide optimal pacing during periods of exercise. In some examples, a previously optimized set of pacing parameters may be implemented when the threshold is crossed. In still other examples, the decision to initiate CRT optimization may be based on changes to the EGM and/or heart sound signals as determined by the cardiac signal analyzer 80. For example, one or more acoustic cardiographic metrics being monitored may pass a pre-defined threshold, thereby triggering the start of a CRT optimization protocol. The decision may also be made based on a combination of one or more of time, activity and changes in cardiac signals. For example, the processor 70 may initiate a CRT optimization protocol after a predetermined period to time if the CRT optimization protocol has not been initiated based on passing an activity level threshold, or based on a change in one or more acoustic cardiographic metrics. In some examples, the CRT optimization protocol may be initiated after a period of time has passed when another event occurs. For example, predefined period of time has passed, the next time the activity level indicates the patient is at rest, for example, the CRT optimization protocol is initiated. If processor 70 does not implement a CRT optimization protocol, the IMD 16 continues to deliver therapy based on current pacing parameters and continues to monitor EGM and heart sound signals (104).

If the processor 70 determines a CRT optimization protocol should be implemented, one or more pacing parameters to be varied during the protocol as well as one or more acoustic cardiographic metrics to be studied may be chosen (106). The pacing parameter(s) chosen may be one or more of: AV delay, VV delay, electrode delivering stimulation, frequency of stimulation, strength of stimulation, lead placement (or pacing site selection), or pacing vector configuration. The choice of parameters may be preselected, may be made based on physician input, or based on which acoustic cardiographic metric has changed, for example. Similarly, the metrics to be studied during the CRT optimization protocol may be preselected, may be made based on physician input, or based on which acoustic cardiographic metric has changed.

Figure 11:
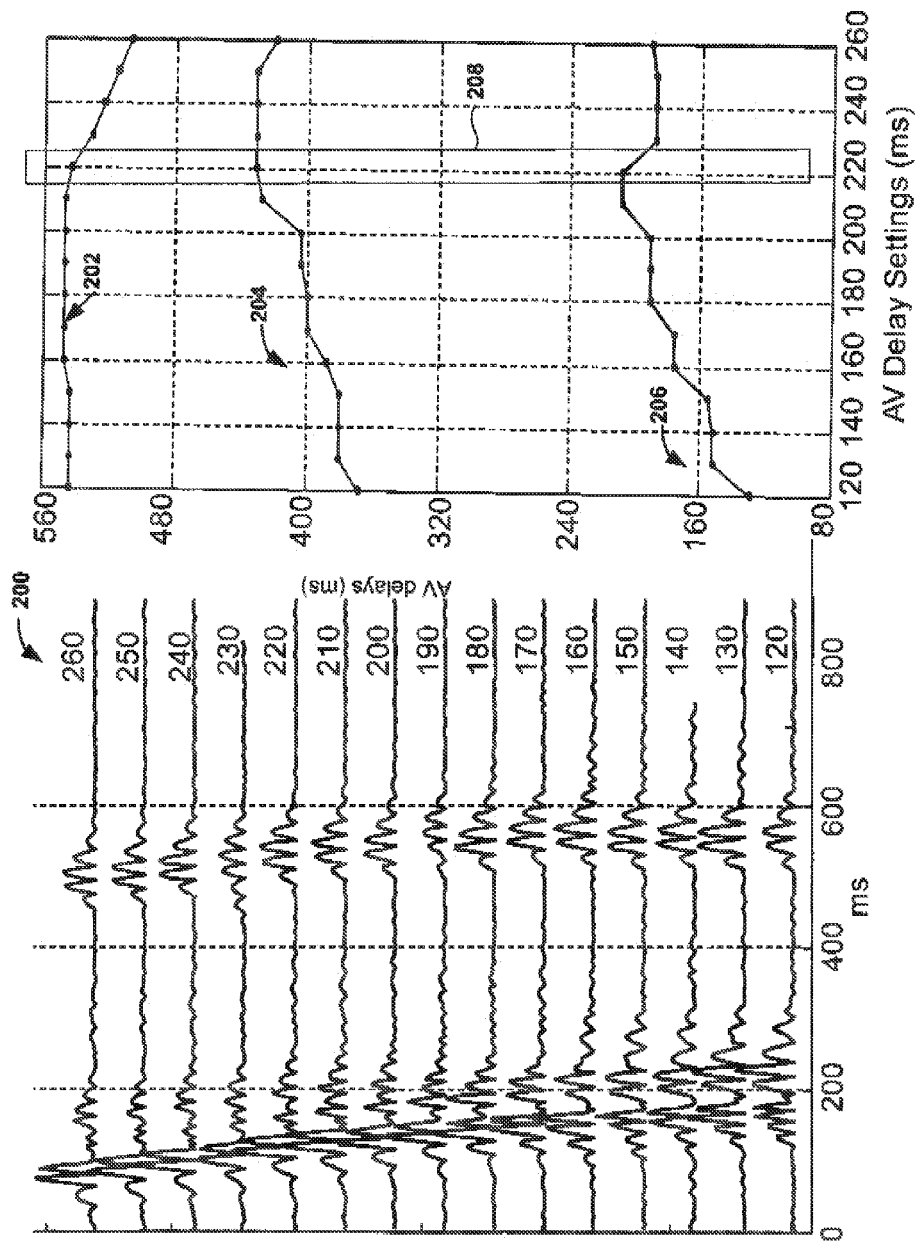
FIG. 11 illustrates the heart sound responses and acoustic cardiographic metric responses for an exemplary CRT optimization protocol.

Heart sound signals and EGM waveforms are collected for each setting tested (108). The pacing parameters may be changed to manipulate AV delay to explore optimal CRT pacing parameters. For example, heart sound signals and EGM waveforms may be collected for a plurality of AV delays. As shown in FIG. 11, discussed in more detail below, pacing may be delivered for AV delays from 120 ms to 260 ms increasing at 10 ms increments. For each tested AV delay heart sound signals and EGM waveforms are collected and stored.

The cardiac signal analyzer 80 and/or processor 70 extract heart sounds and EGM information from the heart sound signals and EGM signals (110). The particular heart sound information that is extracted may be based on the acoustic cardiographic metrics of interest. Similarly, the EGM information extracted is also based on the acoustic cardiographic metrics chosen. In addition, an acoustic cardiographic metric ranking scheme is chosen (112). The ranking scheme can be preset. In other examples, multiple ranking schemes are stored in memory 72, and each ranking scheme is associated with a change in a particular acoustic cardiographic metric. For example, if the CRT optimization protocol was implemented based on a change in S3 amplitude, then the ranking scheme associated with a change in S3 amplitude may be chosen. In this example, the S3 metric may be given the most weight by the ranking scheme followed by other acoustic cardiographic metrics normally affected by changes to heart function when S3 changes. The use of a ranking scheme allows the processor 70 to determine which of the plurality of pacing settings tested should be chosen in the case where there is not a single set of pacing parameters, or setting such as AV delay, that results in maximum performance for every acoustic cardiographic metric studied. Using the extracted heart sound and EGM information the acoustic cardiographic metric results for each setting are reviewed (114) and compiled by processor 70. Then, based on the data and the ranking scheme, a new set of pacing parameters is chosen (116).

In various examples the choice of pacing parameter and acoustic cardiographic metrics are preselected by a physician, for example. As illustrated in FIG. 11, effectiveness of the pacing stimulation provided may be studied for a range of AV delays using multiple acoustic cardiographic metrics. If, as in the example in FIG. 11, a particular AV delay results in the better results for each of the acoustic cardiographic metrics being monitored, then that pacing parameter value (in example in FIG. 11 AV delay) is considered more effective and is chosen for implementation. That is, IMD 16 is programmed to provide therapy based on a set of pacing parameters including the chosen pacing parameter value. If, however, the test of various AV delay values does not result in a particular AV delay optimizing all acoustic cardiographic metrics being monitored, a ranking scheme may be used to choose between various sets of pacing parameters. In some examples, the particular acoustic cardiographic metric may be given the highest priority. The field of possible pacing parameter sets (or AV delays in the example in FIG. 11 are then narrowed to all sets resulting in the best (highest or lowest depending on nature of the metric, for example) value for the high priority metric. If there is still more than one pacing parameter set that results in this value, the remaining pacing sets may further narrowed by a second metric. The process is continued until only one set of pacing parameters remains.

Reviewing the acoustic cardiographic metrics may allow for the determination of a variety of pacing parameters. For example, the CRT optimization protocol may be used to suggest optimal pacing sites, i.e., locations for placement of pacing electrodes, or indicate a choice between previously placed electrodes. For example, the CRT optimization protocol may determine which of electrodes 4, 40, 42, 44, 46, 48, 50, 62, 64 and 66 is used to deliver electrical stimulation to the heart. The CRT optimization may also be used to determine appropriate AV delays, VV delays, pacing vectors, or strength of electrical stimulation. In some examples, the appropriate AV delay may be set within a fusion band in order to provide the patient 14 with fusion pacing.

In various embodiments, IMD 16 provides pacing therapy according to the new set of pacing parameters. IMD 16, including heart sound sensor 82 and sensing module 76 continue to monitor EGM and heart sound signals. Based on the monitored signals, IMD 16 may begin a subsequent CRT optimization protocol in response to a change in one or more acoustic cardiographic metric.

Figure 6:
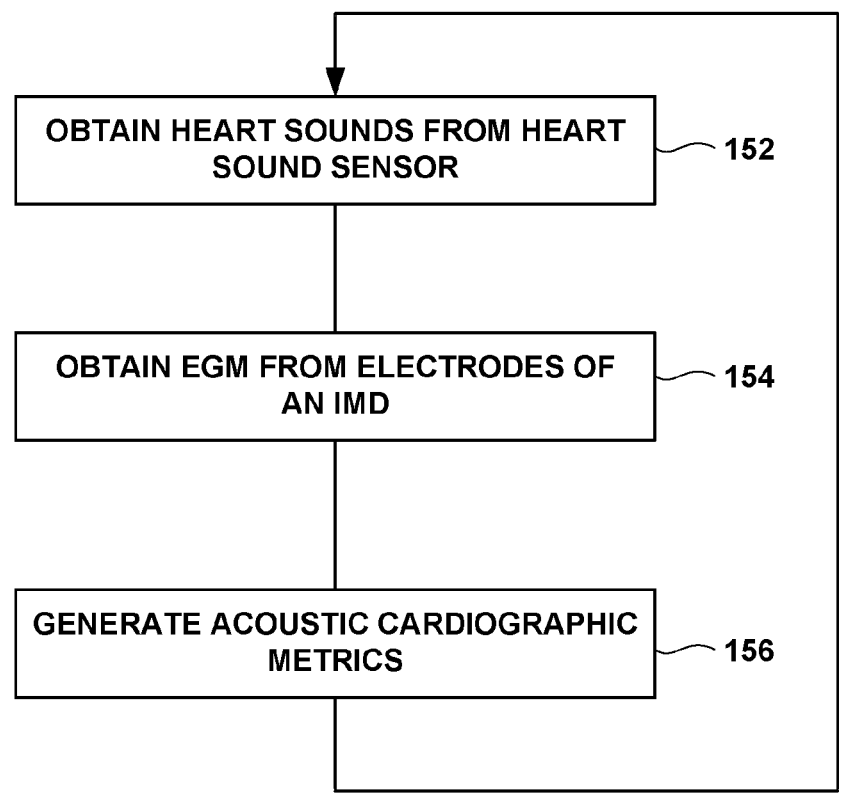
FIG. 6 is a flow chart illustrating an exemplary mode of operation for the IMD of FIG. 1.

FIG. 6 is a flow chart illustrating an example mode of operation of IMD 16. IMD 16 obtains heart sounds using heart sound sensor 82 (152). IMD 16 obtains an EGM signal or more from one or more of electrodes 4, 42, 44, 46, 48, 50, 62, 64 and 66 using sensing module 76 (154). Based on the collected heart sounds and EGM signals IMD 16 generates at least one acoustic cardiographic metric (156).

The acoustic cardiographic metrics may include, for example, an indication of atrioventricular (AV) dyssynchrony based on at least an interval from heart sound S2 to heart sound S1. IMD 16 may generate an acoustic cardiographic metric that is an indication of interventricular (VV) dyssynchrony based on splitting of each of heart sound S1 and heart sound S2. In some embodiments the IMD 16 may generate an acoustic cardiographic metric that is an indication of left intraventricular dyssynchrony based on electromechanical activation delay (EMAT). In other examples, the indication of left intraventricular dyssynchrony may be based on an aortic pre-ejection interval. In some examples, the indication left intraventricular dyssynchrony may be based on the duration of heart sound M1. In other examples, the indication of left intraventricular dyssynchrony may be based on the duration of heart sound A2.

In various examples the acoustic cardiographic metric may be a surrogate for a myocardial performance index (MPI) and be based at least in part on the duration of heart sound S1 and the duration of heart sound S2. The acoustic cardiographic metric may also be an indication of left ventricular (LV) fill time and be based on the interval between heart sound S2 and heart sound S1. In other examples, the acoustic cardiographic metric may be an indication of LV contractility. The acoustic cardiographic metric may be based on the ratio of EMAT plus heart sound S1 duration divided by the interval between heart sound S1 and heart sound S2, or the ratio of EMAT plus S1 duration divided by an R to R interval of the EGM signal.

In certain examples, one or more of the acoustic cardiographic metrics is then used to assess a set of pacing parameters, determine whether a CRT optimization protocol should be initiated, and implement the CRT optimization protocol. In some examples, the CRT optimization protocol may be consistent with the CRT optimization protocol illustrated in FIG. 5. In various examples, IMD 16 continues to monitor heart sound and EGM signals in a continuous manner. In other examples, IMD 16 monitors and obtains heart sounds and/or EGM signals as predetermined intervals. For example, ever hour, every day, every week, etc.

Figure 7:
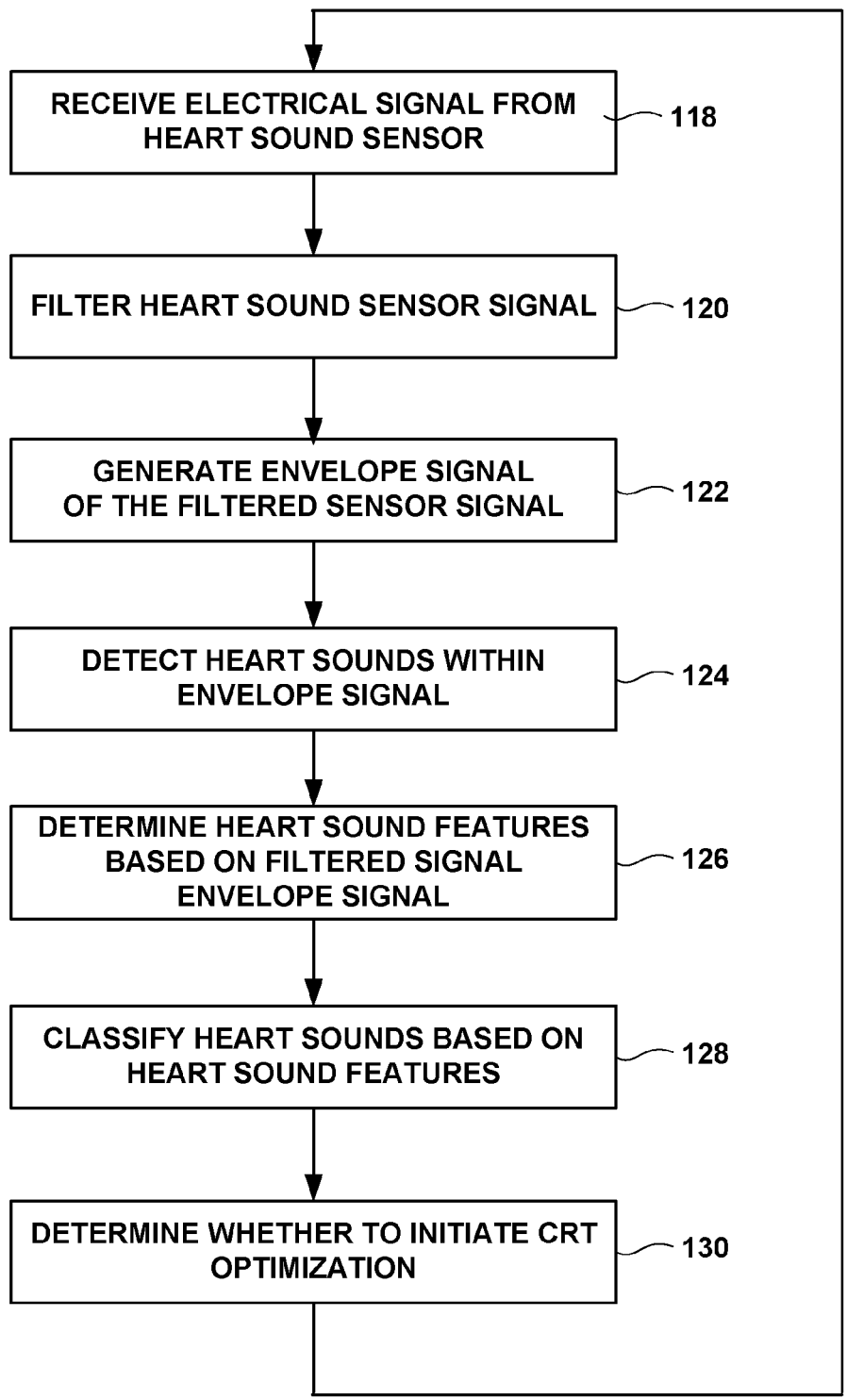
FIG. 7 is a flow diagram illustrating an exemplary method to determine whether or not to initiate a CRT optimization protocol based on detection and classification of heart sounds.

FIG. 7 is a flow diagram illustrating an example method to determine whether or not to initiate a CRT optimization protocol based on detection and classification of heart sounds. The example method is described with respect to heart sound analyzer 80 and its components, and processor 70, but it should be understood that the exemplary method may be performed by any one or more devices, processors, or components described herein.

According to the exemplary method, cardiac signal analyzer 80 receives an electrical signal from heart sound sensor 82 (118). Cardiac signal analyzer 80 or another component of IMD 16 filters (e.g., band pass filter), the heart sound signal (120). Envelope extractor 90 receives the filtered sensor signal and processes the sensor signal to generate the envelope signal of the filtered sensor signal (122).

Heart sound detector 92 detects heart sounds within the envelope signal (124). In some examples, heart sound detector 92 detects the heart sounds using an algorithm that uses and adaptive decaying threshold. Detecting the heart sound within the envelope signal may include marking the heart sounds in time. In some examples, the heart sound detector 92 detects hearts sounds from a signal of heart sounds averaged over period of time.

Heart sound feature module 94 determines heart sound features for the detected heart sounds based on the envelope signal and the filtered heart sound signal (126). For example, heart feature module may determine an MPR and MS for the detected heart sounds. In other examples, the heart sound feature module 94 may determine a heart sound feature, such as the interval between S2 and 51 based on an aspect of heart function of interest. The heart function to be monitored may be determined based on the patient's diagnosis, for example. Classification module 96 classifies each of the detected heart sounds as either normal or abnormal based on the heart sounds features (128). As an example, classification module 96 may compare the MPR and MS of a detected heart sound to a predetermined range of values. In other examples chosen heart sound features are compared to a predetermined threshold.

Indication module 98 provides an indication to processor 70 of whether one or more acoustic cardiographic metrics are considered normal. The indication module makes this determination based on the classification of the studied heart sounds in combination with chosen EGM signals from signal processor 100. For example, indication module 98 may indicate that an acoustic cardiographic metric indicative of LV contractility is outside of predetermined range. Processor 70 determines whether to initiate CRT optimization (130) based on the classification of the heart sounds. In some examples, the determination (130) is made based on heart sound classification in combination with information from the EGM signal, e.g., based on the acoustic cardiographic metric indications from indication module 98. If processor 70 does not decide to initiate CRT optimization, IMD 16 continues to provide pacing therapy under the same set of cardiac pacing parameters.

Figure 8:
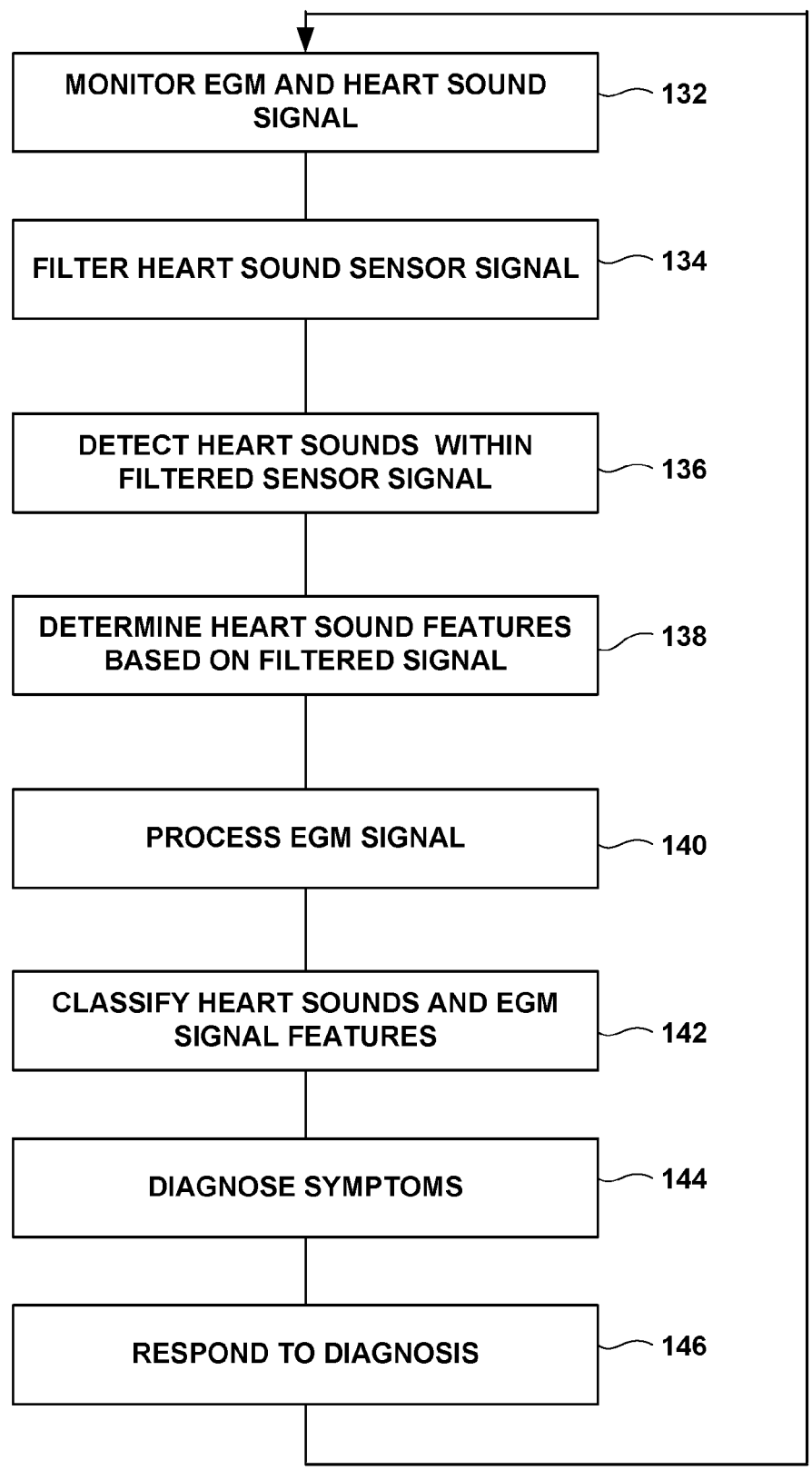
FIG. 8 is a flow diagram illustrating an exemplary method of diagnosing a patient based on heart sounds collected in an IMD.

FIG. 8 is a flow diagram illustrating an example method of diagnosing a patient based on heart sounds collected by IMD 16. Sensing module 76 and heart sound sensor 82 monitor EGM and heart sound signals, respectively (132). The signals from sensing module 76 and heart sound sensor 82 can be processed continuously, or at predetermined intervals. In some examples, the signals are averaged over a period of time. The averaging of the signal can occur before or after the heart sound signal is passed to cardiac signal analyzer 80. Cardiac signal analyzer 80 or another component of IMD 16 filters (e.g., band pass filter), the heart sound signal (134). The filtered signal is provided to heart sound detector 92 which detects heart sounds within the filtered heart sound signal (136). In some examples, heart sound detector 92 detects the heart sounds using an algorithm that uses and adaptive decaying threshold.

Heart sound feature module 94 determines heart sound features for the detected heart sounds based the filtered heart sound signal (138). For example, heart feature module may determine an MPR and MS for the detected heart sounds. In other examples, the heart sound feature module 94 may determine a heart sound feature, such as the splitting time between A2 and P2, which correlates to pulmonary hypertension. The features extracted from the heart sound signal may be chosen based on the disease being diagnosed. The sensing module 76 provides an EGM signal covering the same time period as the heart sound signal to EGM signal processor 100 and/or processor 70. EGM signal processor 100 processes the EGM signal 100 to extract features of the EGM signal (140). For example, the processing of the EGM signal may result in information regarding RR interval, QRS duration, PR interval, and/or QT interval.

Classification module 96 classifies the heart sound features extracted by heart sound feature module 94. In some examples, the classification is provisionally depending on a comparison to various EGM features in indication module 98. In other examples classification module 96 classifies both heart sounds features and EGM features (142), alone or in combination with one another.

In other examples, the processed EGM signal is provided to classification module 96 and acoustic cardiographic metrics based on one or both of the heart sound features and the EGM features are classified. Indication module 98 provides an indication to processor 70 of whether the acoustic cardiographic metrics studied are normal or abnormal. For example, indication module 98 may indicate that one or more acoustic cardiographic metrics is outside a predetermined range, and therefore is abnormal.

Processor 70 diagnoses symptoms with the current functioning of the heart based on the one or more acoustic cardiographic metric indicators received. The processor may determine that the electrical or mechanical function that is outside of the normal range is indicative of a particular disease. For example, the processor 70 may determine that the patient 14 is suffering from hypertension. After a diagnosis of the symptoms has been made IMD 16 responds to the diagnosis (146). In some examples, the processor 70 provides an indication of the diagnosis to programmer 24 via telemetry module 78. Telemetry module 78 may communicate with programmer 24 or another external device to provide the information to a physician, for example. In other examples, the processor 70 provides telemetry module 78 with information regarding which functions of the heart are not functioning normally without providing a final diagnosis. The information is provided by telemetry module 78 to a physician or other clinician via programmer 24 or another external device in communication with telemetry module 78. In some examples the processor initiates a CRT optimization protocol to determine a set of pacing parameters that treat the abnormal functions of the heart. In some examples, the acoustic cardiographic metrics are used to help set an AV interval provided by the pacing in order to provide fusion pacing to patient 14 in response to the diagnosis.

Figure 9:
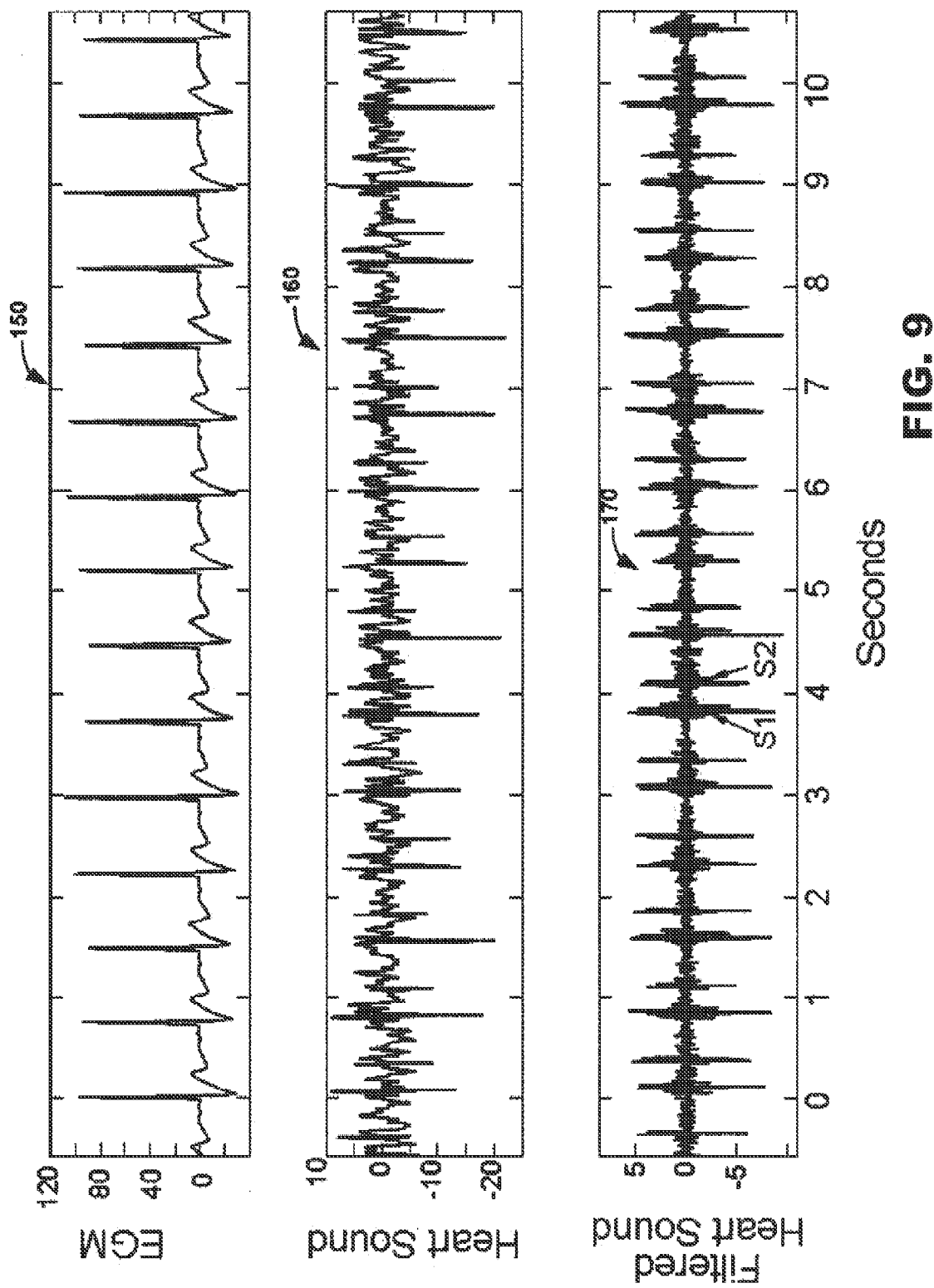
FIG. 9 illustrates exemplary heart sounds and EGM signals.

FIG. 9 illustrates example heart sound and EGM signals. EGM signal 150, heart sound signal 160, and filtered heart sound 170 are aligned in time. EGM signal 150 is detected by sensing module 76. Heart sound signal 160 is detected by heart sound sensor 82, and filtered heart sound signal 170 is the result of filtering in heart sound detector 92, for example.

Figure 10:
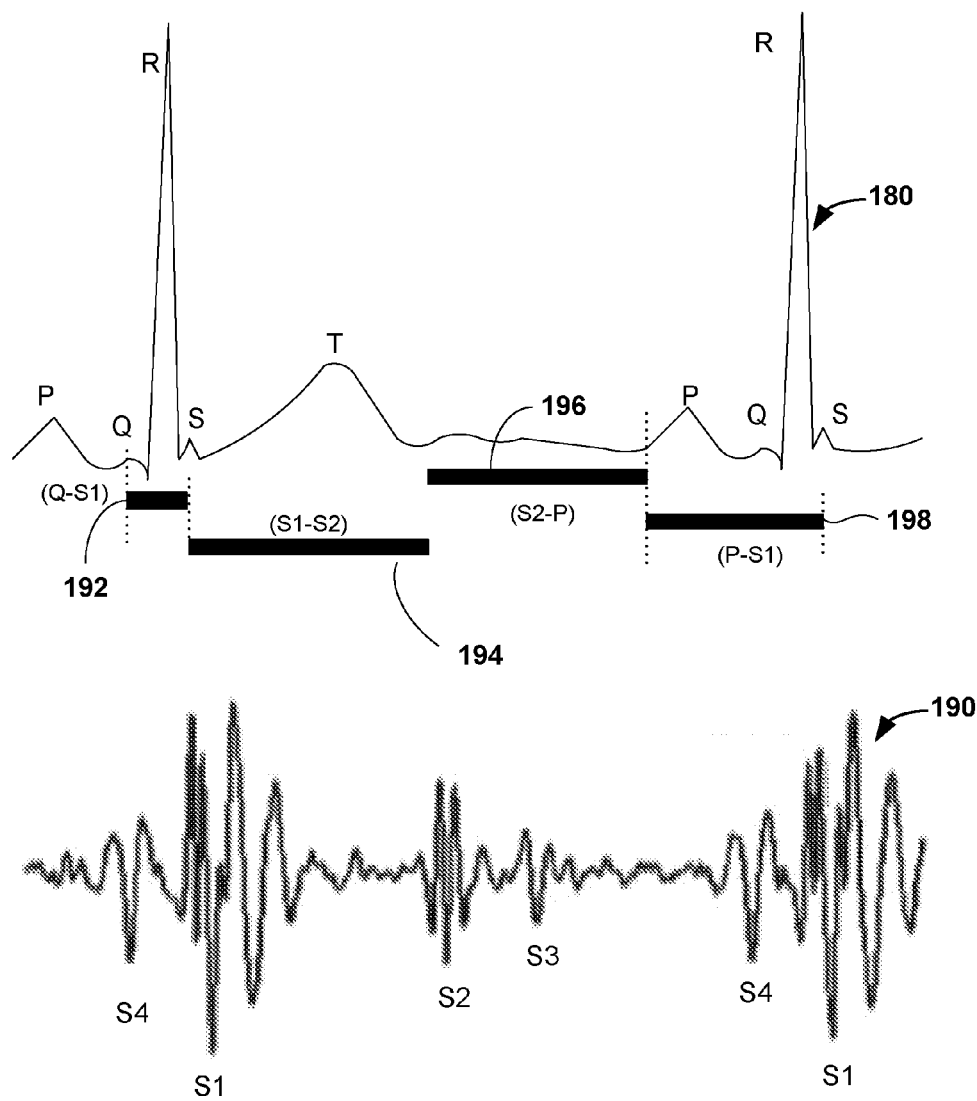
FIG. 10 illustrates the heart sound features and EGM signal features used in various acoustic cardiographic metrics.

FIG. 10 illustrates the heart sound features and EGM signal features used in various acoustic cardiographic metrics. Heart signal 190 is labeled to show heart sounds S1-S4. EGM tracing 180 is labeled to show the P wave, QRS complex and T wave of the electrical signal. FIG. 10 also illustrates a number of acoustic cardiographic metrics. For example, electromechanical activation time (EMAT) 192 can be approximated by the interval between Q of signal 180 and S1 of signal 190. The Q-S1 interval is a surrogate for the max change rate in LV blood pressure. An increase Q-S1 interval indicates a decrease in the max change rate in pressure. In some examples, EMAT is normalized by an R to R interval, that is, the R to R interval is used to remove variation based on current heart rate. The S1-S2 interval is a surrogate for stroke volume, i.e., Left Ventricular Systolic Time (LVST) 194. A decreased S1-S2 interval equates to a decreased stroke volume. In some examples, LVST is normalized by the R to R interval. Pre-atrial filling time (PAFT) 196 is determined based on the interval between heart sound S2 and the P wave of the EGM (or ECG) signal. The accelerated atrial filling time (AAFT) 198 is determined based on the interval between the P-wave of the EGM (or ECG) signal and heart sound S1. In addition, the presence of either heart sound S3 or S4 indicates left ventricle dysfunction. The intensity, and pervasiveness, of heart sounds S3 or S4 further indicates the level of dysfunction present. One or more of the illustrated acoustic cardiographic metrics may be used in determining whether to initiate CRT optimization, or which of a plurality of tested pacing parameter settings to implement.

Figure 12:
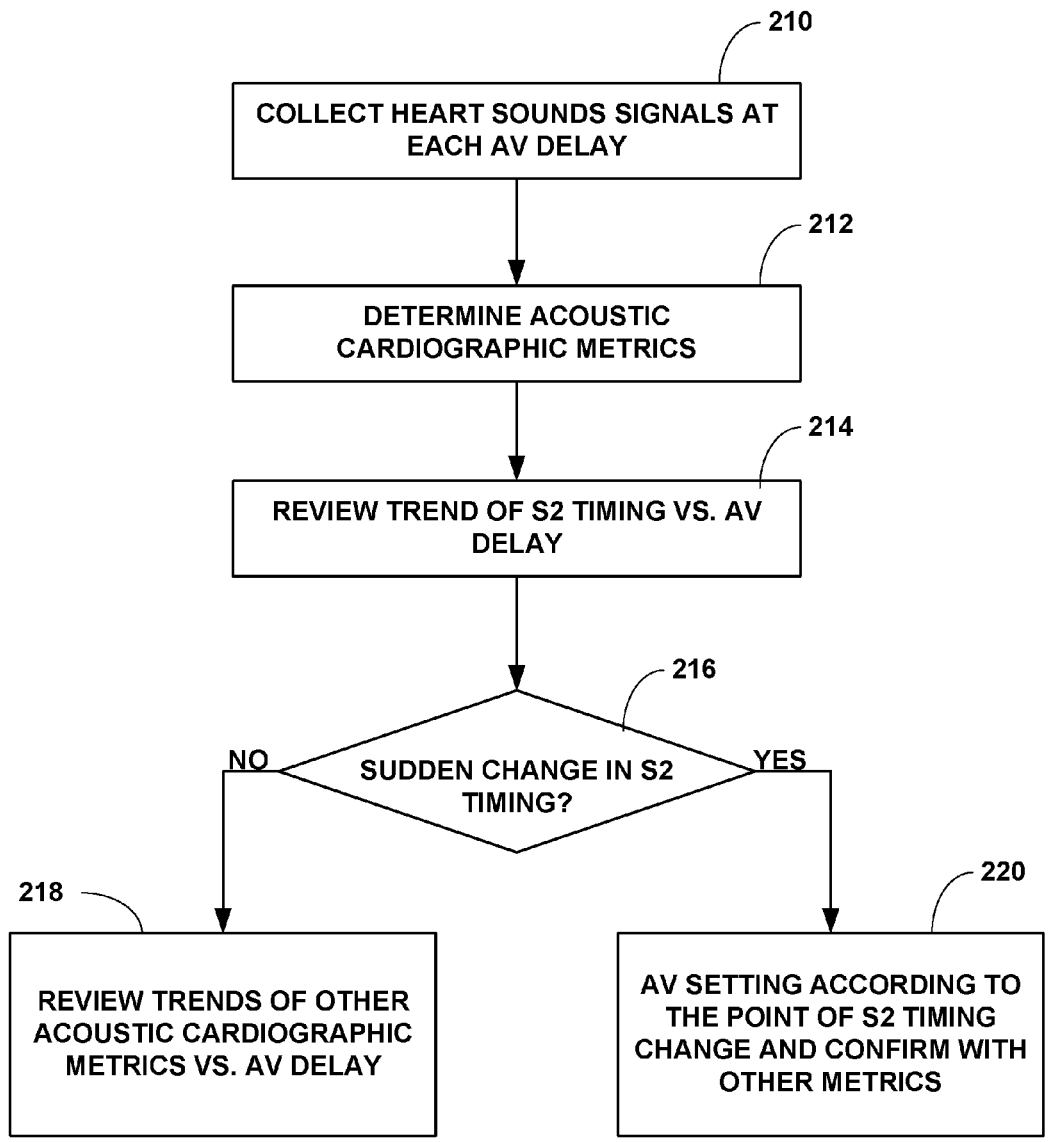
FIG. 12 illustrates an exemplary CRT optimization protocol using AV delay adjustments.

FIG. 11 illustrates the heart sound responses and acoustic cardiographic metric responses for an exemplary CRT optimization protocol. In this example, the AV delay pacing parameter is optimized. In some examples, the heart sounds signals 200 are used in a method as illustrated in FIG. 12, and discussed in more detail below. In some examples, Processor 70 varies the AV delay of the signals sent to the electrodes by signal generator 74. The processor 70 starts the signal at an AV delay of 120 ms and increases the AV delay of the signal by 10 ms up to an AV delay of 260. For each new AV delay, a heart sound signal is collected by heart sound sensor 82 and an EGM signal is collected by sensing module 76. In the example, three acoustic cardiographic metrics, 202, 204 and 206 are measured for each AV delay. In this example acoustic cardiographic metrics 202, 204, and 206 indicate better heart function with higher values of the acoustic cardiographic metric. In this example, acoustic cardiographic metric 202 is S2 timing. The timing is determined based on how long after the pacing pulse S2 occurs. Acoustic cardiographic metric 204 is a systolic time interval (STI). In some examples the STI is LVST and is the interval between S1 and S2. Acoustic cardiographic metric 206 is S1 amplitude. After the acoustic cardiographic metrics for each AV delay are collected, the desired AV delay is chosen based on which AV delay results in the most acoustic cardiographic metrics as close to the highest value recorded for the acoustic cardiographic metric. In this example, a 220 ms AV delay is ideal, and is highlighted by box 208. In some examples, a new set of pacing parameters would be applied after the AV optimization using an AV delay of 220 ms.

FIG. 12 illustrates an exemplary CRT optimization protocol using AV delay adjustments. FIG. 11 illustrates and example of results collected using the method disclosed with respect to FIG. 12. IMD 16 collects heart sounds signals at each AV delay (210) that is being tested. In some examples, the AV delays may range from 120 ms to 260 ms, at 10 ms intervals. IMD 16 extracts information from the heart sounds signal that is used to determine acoustic cardiographic metrics (212) for each heart sound signal at each AV delay. In some examples, cardiac signal analyzer 80 extracts information from the heart sound signals used by processor 70 to determine the values of various acoustic cardiographic metrics. In some examples, the acoustic cardiographic metrics of interest include S2 timing. In some examples, IMD 16 reviews trends of S2 versus AV delay (214). In some examples, IMD 16 transmits, via telemetry module 78, the heart sound signals or the acoustic cardiographic metrics of interest to a remote device. In some cases, the acoustic cardiographic metrics, including S2 timing are displayed on a remote device, and a physician reviews the values for S2 timing versus AV delay (214). Based on the review of S2 timing the reviewer determines if there was a sudden change in S2 timing (216). If there has not been a sudden change in S2 timing, the trends of other acoustic cardiographic metrics versus the different AV delays are reviewed (218). In some examples, IMD 16 reviews the acoustic cardiographic metrics. IMD 16 may determine at which AV delay each acoustic cardiographic metric is optimized. As shown in FIG. 11, IMD 16 may determine at which AV delay the most acoustic cardiographic metrics have the best value achieved from the AV delays tested. In some examples, when there is no AV delay value that results in each of the monitored acoustic cardiographic metrics having their best values, IMD 16 chooses the AV delay with the most acoustic cardiographic metrics optimized. In some examples, a specific acoustic cardiographic metric may be given greater weight than other acoustic cardiographic metrics. For example, if there has been a sudden change in S2 timing then, the IMD implements a set of pacing parameters that includes using AV delay setting according to the point of S2 timing change. The AV delay setting is then confirmed with other metrics (220). The confirmation ensures that the other cardiac metrics being monitored, for example, S1 amplitude and STI are within a predetermined range of their respective best values.

As discussed above, a variety of physiologically relevant information, represented by acoustic cardiographic metrics, may be used to help a CRT device improve cardiac function through the modification of pacing parameters. For example, the pacing parameters may be modified by processor 70 to minimize the interval between S3 and S4, without fusing them, to avoid a collision of the early (E) wave and Atrial (A) wave, as seen on an echocardiogram. This may be done by modifying AV delays to find the optimal AV delay setting.

In other examples, the modification of pacing parameters may be directed at trying to make sure the interval between S2 and S1 is greater than 40% of an EGM R to R interval. This ensures that the heart has enough left ventricular filling time to function properly. The modification of a pacing parameter, for example, AV delay in dual-chamber devices, sensed and pacing AV and VV delays in triple-chamber devices, rate-response parameters, parameters for Rate-Adaptive AV delay feature, parameters for pacing vector, parameters for pacing strength, and other parameters for Adaptive CRT, by processor 70 may provide changes to the interval between S2 and S1. For example, S2 detection could assure that that a pacing stimulus was not applied until a period of time after cardiac relaxation began to avoid impairment of diastole and therefore the risk for severely reduced diastolic cardiac perfusion. It can measure the filling interval of the ventricle to avoid rates that would inappropriately restrict filling.

In some examples, the modification of pacing parameters by processor 70 may be directed to trying to optimize the S1 splitting between M1 and T1 and/or the S2 splitting between A2 and P2. In some examples, the smaller the split between the times, the more in sync the contraction of the ventricles. In some examples, a patient may have a natural physiologic split within S1 or S2. The optimal split in S1 may be up to 40 ms and the optimal split for S2 may be up to 20 ms. The modification of the pacing parameter VV delay by processor 70 may help minimize the splitting of S1 and/or S2, which in turn may improve VV synchrony to enhance cardiac output.

In other examples, the modification of pacing parameters may be directed to minimizing the sum of (S1 duration+S2 duration) or the ratio (S1 duration+S2 duration)/(interval between S1 and S2). These metrics may act as a surrogate for the myocardial performance index, and may be used to maximize both systolic and diastolic functioning of the heart. The modification of the pacing parameters AV delay and VV delay by processor 70 may help minimize the surrogates for the myocardial performance index and thereby help maximize both systolic and diastolic functioning of the heart.

In some examples, the modification of pacing parameters by processor 70 is directed to minimizing the aortic pre-ejection interval in order to maximize left ventricle contractility. A number of acoustic cardiographic metrics may be used to approximate the aortic pre-ejection interval including, EMAT+S1 duration, the ratio of (EMAT+S1 duration)/(interval between S1 and S2), or the ratio of (EMAT+S1 duration)/(EGM RR interval). The modification of pacing parameter AV delay may help minimize the aortic pre-ejection interval.

In other examples, the modification of pacing parameters by processor 70 is directed to minimizing S1 acceleration time (from onset to first maximum peak) to minimize mitral valve late diastolic regurgitation. The modification of the pacing parameter AV delay may help minimize S1 acceleration time and thereby minimize mitral valve late diastolic regurgitation.

In some examples, the modification of pacing parameters is directed to minimizing the amplitude and duration of S3. The presence of heart sound S3 usually indicates a failing left ventricle and is associated with elevated left ventricle filling pressure. The modification of the pacing parameter AV delay by processor 70 may help minimize the presence of heart sound S3.

In other examples, the modification of pacing parameters is directed to minimizing the amplitude and duration of S4. The presence of heart sound S4 is caused by atrial contraction when the left ventricle has lost its compliance, e.g., in acute myocardial infract and ischemia. In some examples S4 may also indicate LV hypertension. The modification of the pacing parameter AV delay may help minimize the presence of heart sound S4.

In various examples, one or more of the above acoustic cardiographic metrics is monitored and optimized based on modifications to one or more pacing parameters. In some examples, interplay between the various pacing parameters is also monitored in order to provide the best overall cardiac functioning.

The techniques described in this disclosure may be implemented, at least in part, in hardware, software, firmware, or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various examples have been described. These and other examples are within the scope of the following claims.

The invention claimed is:

1. A method comprising:
obtaining heart sounds from an implanted heart sound sensor;
obtaining an electrogram (EGM) from electrodes of an implantable device;
generating one or more acoustic cardiographic metrics based on at least one of the heart sounds and the electrogram for a set of cardiac pacing parameters, the set of cardiac pacing parameters including a plurality of pacing parameters;
wherein the acoustic cardiographic metrics include one or more of:
an indication of atrioventricular (AV) dyssynchrony based on at least an interval from heart sound S2 to heart sound S1;
an indication of interventricular (VV) dyssynchrony based on a splitting of at least one of heart sound S1 and heart sound S2;
an indication of left intraventricular dyssynchrony based on at least one of electromechanical activation delay (EMAT),
EMAT plus S1 duration,
heart sound M1 duration, and
heart sound A2 duration,
a surrogate for a myocardial performance index (MPI) based at least on a duration heart sound S1 and a duration of heart sound S2;
an indication of left ventricle (LV) fill time based on the interval between heart sound S2 and heart sound S1; and
an indication of LV contractility based on at least one of:
a ratio of EMAT plus heart sound S1 duration divided by the interval between heart sound S1 and heart sound S2;
the ratio of EMAT plus S1 duration divided by an R to R interval of the EGM, or an indication of hypertension based on at least one of:
heart sound S1 splitting and heart sound S2 splitting,
relative changes of intensity of M1 and heart sound T1 over a predetermined period of time,
relative change in a A2 to heart sound P2 amplitude ratio over a predetermined period of time,
variability in Q wave to heart sound A2 interval (Q-A2) over time, or heart sound S4; and
wherein the acoustic cardiographic metric comprising the indication of VV dyssynchrony is based on the splitting of heart sound S1 and heart sound S2, the method further comprising adjusting one or more cardiac pacing parameters to obtain an S1 split between M1 and T1 that is between approximately 20 and 40 ms and an S2 split between A2 and P2 that is approximately 20 ms.

2. A method comprising:
obtaining heart sounds from an implanted heart sound sensor;
obtaining an electrogram (EGM) from electrodes of an implantable device;
generating one or more acoustic cardiographic metrics based on at least one of the heart sounds and the electrogram for a set of cardiac pacing parameters, the set of cardiac pacing parameters including a plurality of pacing parameters;
wherein the acoustic cardiographic metrics include one or more of:
an indication of atrioventricular (AV) dyssynchrony based on at least an interval from heart sound S2 to heart sound S1;
an indication of interventricular (VV) dyssynchrony based on a splitting of at least one of heart sound S1 and heart sound S2;
an indication of left intraventricular dyssynchrony based on at least one of
electromechanical activation delay (EMAT),
EMAT plus S1 duration,
heart sound M1 duration, and
heart sound A2 duration,
a surrogate for a myocardial performance index (MPI) based at least on a duration heart sound S1 and a duration of heart sound S2;
an indication of left ventricle (LV) fill time based on the interval between heart sound S2 and heart sound S1; and
an indication of LV contractility based on at least one of:
a ratio of EMAT plus heart sound S1 duration divided by the interval between heart sound S1 and heart sound S2;
the ratio of EMAT plus S1 duration divided by an R to R interval of the EGM, or
an indication of hypertension based on at least one of:
heart sound S1 splitting and heart sound S2 splitting,
relative changes of intensity of M1 and heart sound T1 over a predetermined period of time,
relative change in a A2 to heart sound P2 amplitude ratio over a predetermined period of time,
variability in Q wave to heart sound A2 interval (Q-A2) over time, or heart sound S4; and
further comprising adjusting one or more cardiac pacing parameters based on the indication of LV filling time to obtain an interval between S2 and S1 that is greater than 40% of an R to R interval of the EGM.

3. The method of claim 2, further comprising evaluating at least one of the cardiac pacing parameters based on at least one acoustic cardiographic metric, the evaluation comprising varying the at least one cardiac pacing parameter over a predetermined range at a predetermined interval and storing a corresponding acoustic cardiographic metric value for each variation of the at least one cardiac pacing parameter, and comparing the stored acoustic cardiographic metric values.

4. The method of claim 2, further comprising providing pacing according to the set of cardiac pacing parameters.

5. The method of claim 4, wherein the pacing includes cardiac resynchronization therapy.

6. The method of claim 2, further comprising evaluating at least one of the indications of hypertension, and based on the evaluation of the at least one indication of hypertension, generating a diagnosis of hypertension.

7. The method of claim 6, further comprising providing the diagnosis of hypertension to a remote device.

8. The method of claim 6, furthering comprising modifying the set of cardiac pacing parameters in response to the diagnosis of hypertension.

9. The method of claim 1, further comprising evaluating effectiveness of the cardiac pacing parameters based on at least one of the acoustic cardiographic metrics.

10. The method of claim 9, further comprising:
generating a first acoustic cardiographic metric value for one of the acoustic cardiographic metrics corresponding to a first parameter value of one of the cardiac pacing parameters;
generating a second acoustic cardiographic metric value for the one of the acoustic cardiographic metrics corresponding to a second parameter value of the one of the cardiac pacing parameters;
comparing the first acoustic cardiographic metric value and the second acoustic cardiographic metric value; and
determining, based on the comparison, which of the first parameter value and the second parameter is more effective.

11. The method of claim 1 further comprising determining, based on the acoustic cardiographic metrics, a fusion band.

12. The method of claim 11, wherein an AV delay pacing parameter is set within the fusion band.

13. The method of claim 1, further including choosing an atrioventricular delay pacing parameter based on a change in heart sound S2 timing.

14. The method of claim 2, further comprising adjusting one or more of the cardiac pacing parameters based on at least one acoustic cardiographic metric.

15. A device comprising:
a heart sound sensor configured to obtain a heart sound signal;
an electrogram (EGM) sensor configured to obtain an electrogram; and
a processor configured to generate one or more acoustic cardiographic metrics based on at least one of the heart sound signal received from the heart sound sensor and the EGM received from the EGM sensor for a set of cardiac pacing parameters, wherein the acoustic cardiographic metrics include one or more of:
an indication of atrioventricular (AV) dyssynchrony based on at least an interval from heart sound S2 to heart sound S1;
an indication of interventricular (VV) dyssynchrony based on a splitting of at least one of heart sound S1 and heart sound S2;
an indication of left intraventricular dyssynchrony based on at least one of
electromechanical activation delay (EMAT),
EMAT plus S1 duration,
heart sound M1 duration, and
heart sound A2 duration, a surrogate for a myocardial performance index (MPI) based at least on a duration heart sound S1 and a duration of heart sound S2;
an indication of left ventricle (LV) filling time based on the interval between heart sound S2 and heart sound S1; and
an indication of LV contractility based on at least one of:
the ratio of EMAT plus heart sound S1 duration divided by the interval between heart sound S1 and heart sound S2;
the ratio of EMAT plus S1 duration divided by an R to R interval of the EGM:
an indication of hypertension based on at least one of:
heart sound S1 splitting and heart sound S2 splitting,
relative changes of intensity of M1 and heart sound T1 over a predetermined period of time,
relative change in a A2 to heart sound P2 amplitude ratio over a predetermined period of time,
variability in Q wave to heart sound A2 interval (Q-A2) over time, or heart sound S4; and
wherein the acoustic cardiographic metric comprises the indication of VV dyssynchrony, and is based on the splitting of heart sound S1 and heart sound S2, and the processor is further configured to one or more cardiac pacing parameters to obtain an S1 split between M1 and T1 that is between approximately 20 and 40 ms and an S2 split between A2 and P2 that is approximately 20 ms.

16. The device of claim 15, wherein the processor is further configured to evaluate the effectiveness of the cardiac pacing parameters based on at least one of the acoustic cardiographic metrics.

17. The device of claim 16, wherein the processor is further configured to:
generate a first acoustic cardiographic metric value for one of the acoustic cardiographic metrics corresponding to a first parameter value of one of the cardiac pacing parameters;
generate a second acoustic cardiographic metric value for the one of the acoustic cardiographic metrics corresponding to a second parameter value of the of the one of the cardiac pacing parameters;
compare the first acoustic cardiographic metric value and the second acoustic cardiographic metric value; and
determine, based on the comparison, which of the first parameter value and the second parameter is more effective.

18. The device of claim 15, wherein the processor is further configured to determined, based on the acoustic cardiographic metrics, a fusion band.

19. The device of claim 18, wherein the processor is further configured to set an AV delay pacing parameter within the fusion band.

20. The device of claim 15, wherein the processor is further configured to choose an atrioventricular delay pacing parameter based on a change in heart sound S2 timing.

21. The device of claim 15, wherein the device is an implantable medical device.

22. The device of claim 15, further comprising means for evaluating at least one of the indications of hypertension and means for generating a diagnosis of hypertension based on the evaluation of the at least one indication of hypertension.

23. The device of claim 22, further comprising means for providing the diagnosis of hypertension to a remote device.

24. The device of claim 22, further comprising means for modifying the set of cardiac pacing parameters in response to the diagnosis of hypertension.

25. A device comprising:
a heart sound sensor configured to obtain a heart sound signal;
an electrogram (EGM) sensor configured to obtain an electrogram; and
a processor configured to generate one or more acoustic cardiographic metrics based on at least one of the heart sound signal received from the heart sound sensor and the EGM received from the EGM sensor for a set of cardiac pacing parameters, wherein the acoustic cardiographic metrics include one or more of:
an indication of atrioventricular (AV) dyssynchrony based on at least an interval from heart sound S2 to heart sound S1;
an indication of interventricular (VV) dyssynchrony based on a splitting of at least one of heart sound S1 and heart sound S2;
an indication of left intraventricular dyssynchrony based on at least one of
electromechanical activation delay (EMAT),
EMAT plus S1 duration,
heart sound M1 duration, and
heart sound A2 duration,
a surrogate for a myocardial performance index (MPI) based at least on a duration heart sound S1 and a duration of heart sound S2;
an indication of left ventricle (LV) filling time based on the interval between heart sound S2 and heart sound S1; and
an indication of LV contractility based on at least one of:
the ratio of EMAT plus heart sound S1 duration divided by the interval between heart sound S1 and heart sound S2;
the ratio of EMAT plus S1 duration divided by an R to R interval of the EGM:
an indication of hypertension based on at least one of:
heart sound S1 splitting and heart sound S2 splitting,
relative changes of intensity of M1 and heart sound T1 over a predetermined period of time,
relative change in a A2 to heart sound P2 amplitude ratio over a predetermined period of time,
variability in Q wave to heart sound A2 interval (Q-A2) over time, or heart sound S4; and
wherein the processor is further configured to adjust one or more cardiac pacing parameters based on the indication of LV fill time to obtain an interval between S2 and S1 that is greater than 40% of an R to R interval of the EGM.

26. The device of claim 25, wherein the processor is further configured to adjust one or more of the cardiac pacing parameters based on at least one acoustic cardiographic metric.

27. The device of claim 25, further comprising memory configured to store acoustic cardiographic metric values, and wherein the processor is further configured to evaluate at least one of the cardiac pacing parameters based on at least one acoustic cardiographic metric, the evaluation comprising:
varying the at least one cardiac pacing parameter over a predetermined range at a predetermined interval,
providing to the memory, for storage, a corresponding acoustic cardiographic metric value for each variation of the at least one cardiac pacing parameter; and
comparing the stored acoustic cardiographic metric values.

28. The device of claim 25, further comprising a signal generator configured to provide pacing according to the set of cardiac pacing parameters.

29. The device of claim 28, wherein the signal generator is configured to provide cardiac resynchronization therapy.

30. The device of claim 25, wherein the processor is further configured to evaluate at least one of the indications of hypertension, and based on the evaluation of the at least one indication of hypertension, generate a diagnosis of hypertensions.

31. The device of claim 30, further comprising a telemetry module configured to provide the diagnosis of hypertension to a remote device.

32. The device of claim 30, wherein the processor is further configured to modify the set of cardiac pacing parameters in response to the diagnosis of hypertension.

33. A method comprising:
obtaining heart sounds from an implanted heart sound sensor;
obtaining an electrogram (EGM) from electrodes of an implantable device;
generating one or more acoustic cardiographic metrics based on at least one of the heart sounds and the electrogram for a set of cardiac pacing parameters, the set of cardiac pacing parameters including a plurality of pacing parameters;
wherein the acoustic cardiographic metrics include an indication of interventricular (VV) dyssynchrony based on a splitting of at least one of heart sound S1 and heart sound S2;
wherein the acoustic cardiographic metric comprising the indication of VV dyssynchrony is based on the splitting of heart sound S1 and heart sound S2, the method further comprising adjusting one or more cardiac pacing parameters to obtain an S1 split between heart sound M1 and heart sound T1 that is between approximately 20 and 40 ms and an S2 split between heart sound A2 and heart sound P2 that is approximately 20 ms.

34. A device comprising:
a heart sound sensor configured to obtain a heart sound signal;
an electrogram (EGM) sensor configured to obtain an electrogram; and
a processor configured to generate one or more acoustic cardiographic metrics based on at least one of the heart sound signal received from the heart sound sensor and the EGM received from the EGM sensor for a set of cardiac pacing parameters, wherein the acoustic cardiographic metrics include an indication of interventricular (VV) dyssynchrony based on a splitting of at least one of heart sound S1 and heart sound S2;
wherein the acoustic cardiographic metric comprises the indication of VV dyssynchrony, and is based on the splitting of heart sound S1 and heart sound S2, and the processor is further configured to one or more cardiac pacing parameters to obtain an S1 split between heart sound M1 and heart sound T1 that is between approximately 20 and 40 ms and an S2 split between heart sound A2 and heart sound P2 that is approximately 20 ms.

35. A method comprising:
obtaining heart sounds from an implanted heart sound sensor;
obtaining an electrogram (EGM) from electrodes of an implantable device;
generating one or more acoustic cardiographic metrics based on at least one of the heart sounds and the electrogram for a set of cardiac pacing parameters, the set of cardiac pacing parameters including a plurality of pacing parameters;
wherein the acoustic cardiographic metrics include an indication of interventricular (VV) dyssynchrony based on a splitting of at least one of heart sound S1 and heart sound S2;
wherein the acoustic cardiographic metric comprising the indication of VV dyssynchrony is based on the splitting of heart sound S1 and heart sound S2, the method further comprising adjusting one or more cardiac pacing parameters to obtain an S1 split between heart sound M1 and heart sound T1 that is between approximately 20 and 40 ms.

36. A device comprising:
a heart sound sensor configured to obtain a heart sound signal;
an electrogram (EGM) sensor configured to obtain an electrogram; and
a processor configured to generate one or more acoustic cardiographic metrics based on at least one of the heart sound signal received from the heart sound sensor and the EGM received from the EGM sensor for a set of cardiac pacing parameters, wherein the acoustic cardiographic metrics include an indication of interventricular (VV) dyssynchrony based on a splitting of at least one of heart sound S1 and heart sound S2;
wherein the acoustic cardiographic metric comprises the indication of VV dyssynchrony, and is based on the splitting of heart sound S1 and heart sound S2, and the processor is further configured to one or more cardiac pacing parameters to obtain an S1 split between heart sound M1 and heart sound T1 that is between approximately 20 and 40 ms.

37. A method comprising:
obtaining heart sounds from an implanted heart sound sensor;
obtaining an electrogram (EGM) from electrodes of an implantable device; generating one or more acoustic cardiographic metrics based on at least one of the heart sounds and the electrogram for a set of cardiac pacing parameters, the set of cardiac pacing parameters including a plurality of pacing parameters;
wherein the acoustic cardiographic metrics include an indication of interventricular (VV) dyssynchrony based on a splitting of at least one of heart sound S1 and heart sound S2;
wherein the acoustic cardiographic metric comprising the indication of VV dyssynchrony is based on the splitting of heart sound S1 and heart sound S2, the method further comprising adjusting one or more cardiac pacing parameters to obtain an S2 split between heart sound A2 and heart sound P2 that is approximately 20 ms.

38. A device comprising:
a heart sound sensor configured to obtain a heart sound signal;
an electrogram (EGM) sensor configured to obtain an electrogram; and
a processor configured to generate one or more acoustic cardiographic metrics based on at least one of the heart sound signal received from the heart sound sensor and the EGM received from the EGM sensor for a set of cardiac pacing parameters, wherein the acoustic cardiographic metrics include an indication of interventricular (VV) dyssynchrony based on a splitting of at least one of heart sound S1 and heart sound S2;
wherein the acoustic cardiographic metric comprises the indication of VV dyssynchrony, and is based on the splitting of heart sound S1 and heart sound S2, and the processor is further configured to one or more cardiac pacing parameters to obtain an S2 split between heart sound A2 and P2 that is approximately 20 ms.

* * * * *